United States Patent
Stephens et al.

(10) Patent No.: US 10,201,350 B2
(45) Date of Patent: Feb. 12, 2019

(54) INFLATABLE IMPLANT

(75) Inventors: W. Patrick Stephens, Santa Rosa, CA (US); Gerald Ray Martin, Windsor, CA (US)

(73) Assignee: TriVascular, Inc., Santa Rosa, CA (US)

( * ) Notice: Subject to any disclaimer, the term of this patent is extended or adjusted under 35 U.S.C. 154(b) by 803 days.

(21) Appl. No.: 12/628,623

(22) Filed: Dec. 1, 2009

(65) Prior Publication Data

US 2010/0076481 A1    Mar. 25, 2010

Related U.S. Application Data

(62) Division of application No. 10/461,853, filed on Jun. 13, 2003, now Pat. No. 7,632,291.

(51) Int. Cl.
*A61M 29/00* (2006.01)
*A61B 17/12* (2006.01)

(52) U.S. Cl.
CPC .. *A61B 17/12113* (2013.01); *A61B 17/12022* (2013.01); *A61B 17/12136* (2013.01); *A61B 17/12159* (2013.01); *A61B 17/12195* (2013.01)

(58) Field of Classification Search
CPC .......... A61B 17/8855; A61B 17/12195; A61B 17/12109; A61B 17/12022;
(Continued)

(56) References Cited

U.S. PATENT DOCUMENTS 3,631,854 A    1/1972  Fryer
3,701,771 A   10/1972  Torsten et al.
(Continued)

FOREIGN PATENT DOCUMENTS

EP    0 441 516    8/1991
EP    0 617 930   10/1994
(Continued)

OTHER PUBLICATIONS

Invitation to Pay Additional Fees dated Jan. 10, 2005 for PCT patent application No. PCT/US2004/018945 filed on Jun. 14, 2004, 4 pages.
(Continued)

*Primary Examiner* — Melanie R Tyson
(74) *Attorney, Agent, or Firm* — Foley & Lardner LLP

(57) ABSTRACT

Described is an inflatable implant suitable for placement in the human body and left there for an indeterminate and potentially lengthy period of time. The implant is one that has a low profile when introduced into the body and a larger profile when it is inflated with one or more filler materials. Depending upon design and use choices the delivered implant may be removable and adjustable in situ in size, position, location, form, and rigidity. Indeed, in some variations, the design of the implant may be such that it may be removed at a potentially fairly lengthy time after implantation. The implant includes at least one bladder wall that generally is at least partially non-elastic (or unexpandable) after the preselected size is reached. The bladder wall will define at least one fillable volume and may form more than one independent fillable volumes. The bladder wall, in some variations, may be partially elastic or expandable to permit adjustment of implant size or configuration after or during delivery. The implant may be used as a supporting structure in a variety of differing body tissues and structures, e.g., in the spine or as a prosthetic in plastic surgery. The implant may also be used in conjunction with other components (often having a springed bias) as a source of movement in controlling the opening of a lumen or duct, that is to say, as a type of on-off valve or as a controlled flow valve. The implant may be used as an occludant within, or adjacent to, a variety of natural or abnormal anatomical body openings, e.g., vascular and genital lumina, aneurysms, ducts, septal
(Continued)

defects, fistulae, esophagus, etc. The wall and filler material may be selected to deliver treatment materials the locale of the implant site or to remove amounts of harmful materials from such a region. The implant may, with an appropriate filler material or bladder wall material, be used in cooperation with an appropriate radio frequency (RF) source to cause the increase of a localized internal temperature and a resulting tissue change such as coagulation, ablation, or the like. Methods of using the implant are also described.

11 Claims, 23 Drawing Sheets

(58) Field of Classification Search
CPC ........ A61B 17/12113; A61B 17/12159; A61B 17/12136; A61F 2/441; A61F 2002/30581
USPC .................. 606/191–194; 604/96.01–98.01; 623/17.11–17.12, 23.68, 11.11
See application file for complete search history.

(56) References Cited

U.S. PATENT DOCUMENTS

| | | | |
|---|---|---|---|
| 4,364,921 A | 12/1982 | Speck et al. | |
| 4,638,803 A * | 1/1987 | Rand | A61B 17/12136 604/175 |
| 4,662,883 A | 5/1987 | Bell et al. | |
| 4,819,637 A | 4/1989 | Dormandy, Jr. et al. | |
| 4,906,244 A * | 3/1990 | Pinchuk et al. | 606/194 |
| 4,932,938 A | 6/1990 | Goldberg et al. | |
| 5,122,113 A * | 6/1992 | Hattler | 604/26 |
| 5,176,698 A * | 1/1993 | Burns et al. | 606/192 |
| 5,222,970 A * | 6/1993 | Reeves | A61B 17/12109 604/164.05 |
| 5,344,451 A | 9/1994 | Dayton | |
| 5,370,691 A | 12/1994 | Samson | |
| 5,507,770 A | 4/1996 | Turk | |
| 5,524,633 A | 6/1996 | Heaven et al. | |
| 5,658,329 A | 8/1997 | Purkait | |
| 5,662,712 A | 9/1997 | Pathak et al. | |
| 5,683,405 A | 11/1997 | Yacoubian et al. | |
| 5,704,893 A | 1/1998 | Timm | |
| 5,720,762 A * | 2/1998 | Bass | A61B 17/0218 606/192 |
| 5,725,568 A | 3/1998 | Hastings | |
| 5,779,672 A | 7/1998 | Dormandy, Jr. | |
| 5,798,096 A | 8/1998 | Pavlyk | |
| 5,823,995 A * | 10/1998 | Fitzmaurice et al. | 604/103.09 |
| 5,827,289 A * | 10/1998 | Reiley et al. | 606/86 R |
| 5,871,537 A | 2/1999 | Holman et al. | |
| 5,935,667 A | 8/1999 | Calcote et al. | |
| 5,941,909 A | 8/1999 | Purkait | |
| 6,036,640 A | 3/2000 | Corace et al. | |
| 6,068,626 A | 5/2000 | Harrington et al. | |
| 6,074,341 A | 6/2000 | Anderson et al. | |
| 6,096,052 A | 8/2000 | Callister et al. | |
| 6,145,505 A | 11/2000 | Nikolchev et al. | |
| 6,176,240 B1 | 1/2001 | Nikolchev et al. | |
| 6,186,978 B1 | 2/2001 | Samson et al. | |
| 6,280,457 B1 | 8/2001 | Wallace et al. | |
| 6,293,960 B1 * | 9/2001 | Ken | A61B 17/12113 606/195 |
| 6,306,081 B1 * | 10/2001 | Ishikawa et al. | 600/127 |
| 6,312,462 B1 | 11/2001 | McDermott et al. | |
| 6,331,191 B1 | 12/2001 | Chobotov | |
| 6,391,538 B1 | 5/2002 | Vyavahare et al. | |
| 6,395,019 B2 | 5/2002 | Chobotov | |
| 6,395,208 B2 | 5/2002 | Herweck et al. | |
| 6,409,749 B1 | 6/2002 | Maynard | |
| 6,419,701 B1 | 7/2002 | Cook et al. | |
| 6,423,032 B2 | 7/2002 | Parodi | |
| 6,443,941 B1 | 9/2002 | Slepian et al. | |
| 6,530,878 B2 | 3/2003 | Silverman et al. | |
| 6,547,767 B1 * | 4/2003 | Moein | 604/264 |
| 6,591,838 B2 | 7/2003 | Durgin | |
| 6,599,275 B1 | 7/2003 | Fischer, Jr. | |
| 6,706,064 B1 | 3/2004 | Anson | |
| 6,958,212 B1 * | 10/2005 | Hubbell | A61L 27/52 424/78.17 |
| 7,695,488 B2 * | 4/2010 | Berenstein | A61B 17/12022 606/191 |
| 2002/0029051 A1 | 3/2002 | Callister et al. | |
| 2002/0156489 A1 | 10/2002 | Gellman et al. | |
| 2002/0161388 A1 * | 10/2002 | Samuels et al. | 606/192 |
| 2002/0177866 A1 * | 11/2002 | Weikel et al. | 606/192 |
| 2003/0018388 A1 | 1/2003 | Comer | |
| 2003/0033017 A1 * | 2/2003 | Lotz | A61F 2/441 623/17.16 |
| 2003/0074084 A1 | 4/2003 | Nakao | |
| 2003/0093107 A1 * | 5/2003 | Parsonage et al. | 606/194 |
| 2003/0236513 A1 | 12/2003 | Schwarz et al. | |

FOREIGN PATENT DOCUMENTS

| | | |
|---|---|---|
| RU | 2029527 | 2/1995 |
| SU | 1217402 | 3/1986 |
| SU | 1237201 | 6/1986 |
| SU | 1237202 | 6/1986 |
| SU | 1273077 | 11/1986 |
| SU | 1318235 | 6/1987 |
| SU | 1342511 | 10/1987 |
| SU | 1389778 | 4/1988 |
| SU | 1457921 | 2/1989 |
| SU | 1482714 | 5/1989 |
| SU | 1560134 | 4/1990 |
| SU | 1586718 | 8/1990 |
| SU | 1650127 | 5/1991 |
| SU | 1732964 | 5/1992 |
| SU | 1768154 | 10/1992 |
| SU | 1812980 | 4/1993 |
| WO | WO 94/25078 | 11/1994 |
| WO | WO 96/40023 | 12/1996 |
| WO | WO 96/40024 | 12/1996 |
| WO | WO 97/19653 | 6/1997 |
| WO | WO 98/26737 | 6/1998 |
| WO | WO 99/03454 | 1/1999 |
| WO | WO 99/15116 | 4/1999 |
| WO | WO 00/13624 | 3/2000 |
| WO | WO 00/44808 | 8/2000 |
| WO | WO 01/13832 | 3/2001 |
| WO | WO 01/13833 | 3/2001 |
| WO | WO 03/105917 | 12/2003 |

OTHER PUBLICATIONS

Mandai, S. et al. (1992). "Direct Thrombosis of Aneurysms with Cellulose Acetate Polymer. Part I: Results of Thrombosis in Experimental Aneurysms," *J. Neurosurgery* 77:497-500.

Sugawara, T. et al. (1993). "Experimental Investigations Concerning a New Liquid Embolization Method: Combined Administration of Ethanol-Estrogen and Polyvinyl Acetate," *Neuro Med. Chir.* (Tokyo) 33:71-76.

Taki, W. et al. (1990). "A New Liquid Material for Embolization of Arteriovenous Malformations," *AJNR* 11:163-168.

Vinters, H.V. et al. (1985). "The Histoxicity of Cyanoacrylate: A Selective Review," *Neuroradiology* 27:279-291.

Volodos, N.L. et al. (1986). "Self-Fixing Synthetic Prosthesis for Endoprosthetics of Vessels," *Vestnik Khigurgii* pp. 123-124, Abstract Only in English.

Volodos, N.L. et al. (1987). "New Balloon Catheter for Dilating Arteries and Installing Prosthesis During Distal Endoprosthetics With Self-Fixing Synthetic Prosthesis," *Thesis of VIIIth Symposium* (Oct. 8-10, 1987), Abstract Only in English, four pages.

Volodos, N.L. et al. (1989)."Clinical Experience in Use of Self-Fixing Synthetic Prosthesis for Distal and Intraoperative Endoprosthetics of Aorta and Iliac Arteries," *Theses of IXth All-Union Symposium* (Oct. 2-3, 1989), Abstract Only in English, four pages.

Wisselink, W. et al. (2001). "Clipping of Inferior Mesenteric and Lumbar Arteries via Retroperitoneal Laparo-Endoscopic Approach

(56) References Cited

OTHER PUBLICATIONS as a Treatment of Persistent Endoleak" Chapter 18 *In Endoleaks and Endotension*, Veith, F.J. et al. eds. Marcel Dekker, Inc. pp. 211-220.
Final Office Action dated Feb. 24, 2014 for U.S. Appl. No. 12/566,104.

* cited by examiner

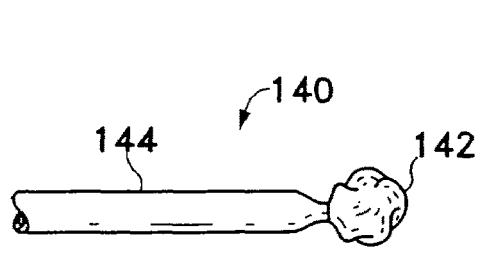
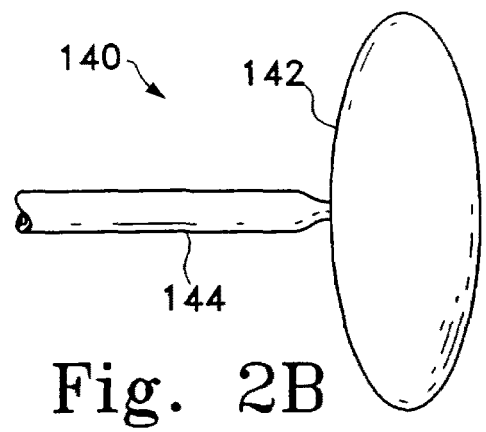
Fig. 2A          Fig. 2B
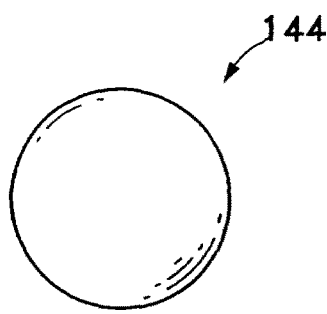
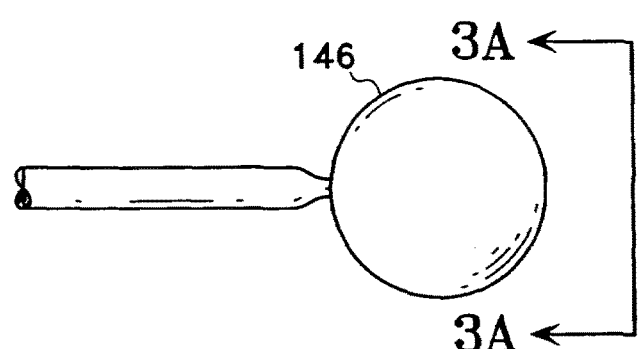
Fig. 3A          Fig. 3B
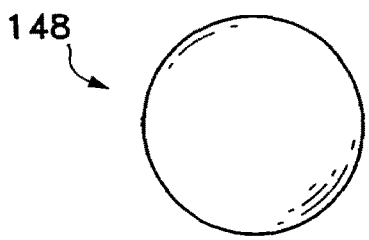
Fig. 4A
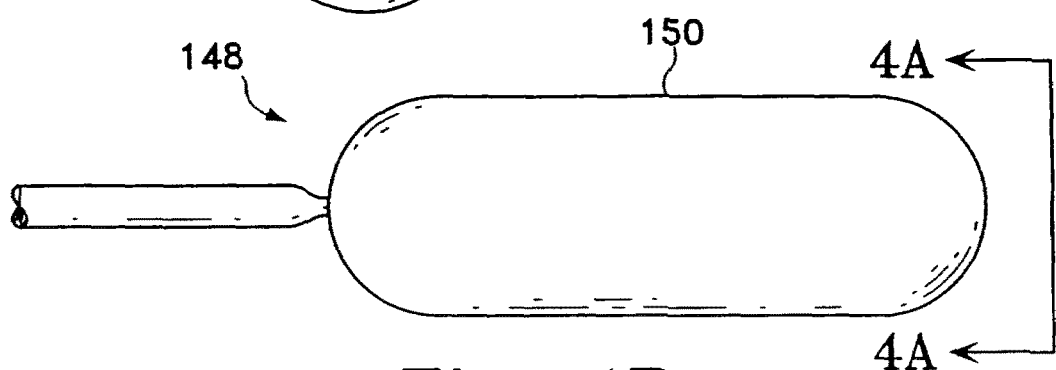
Fig. 4B

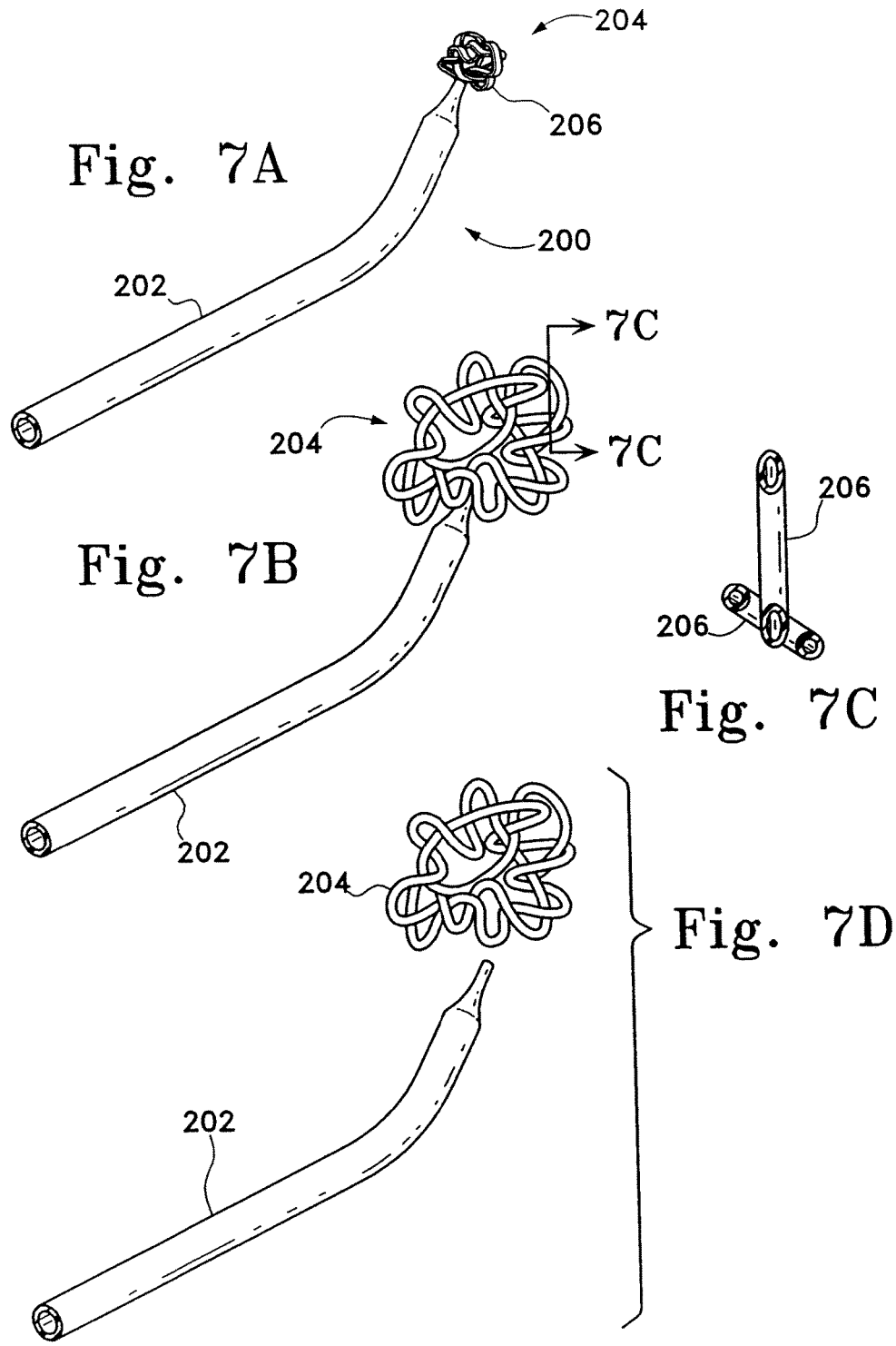

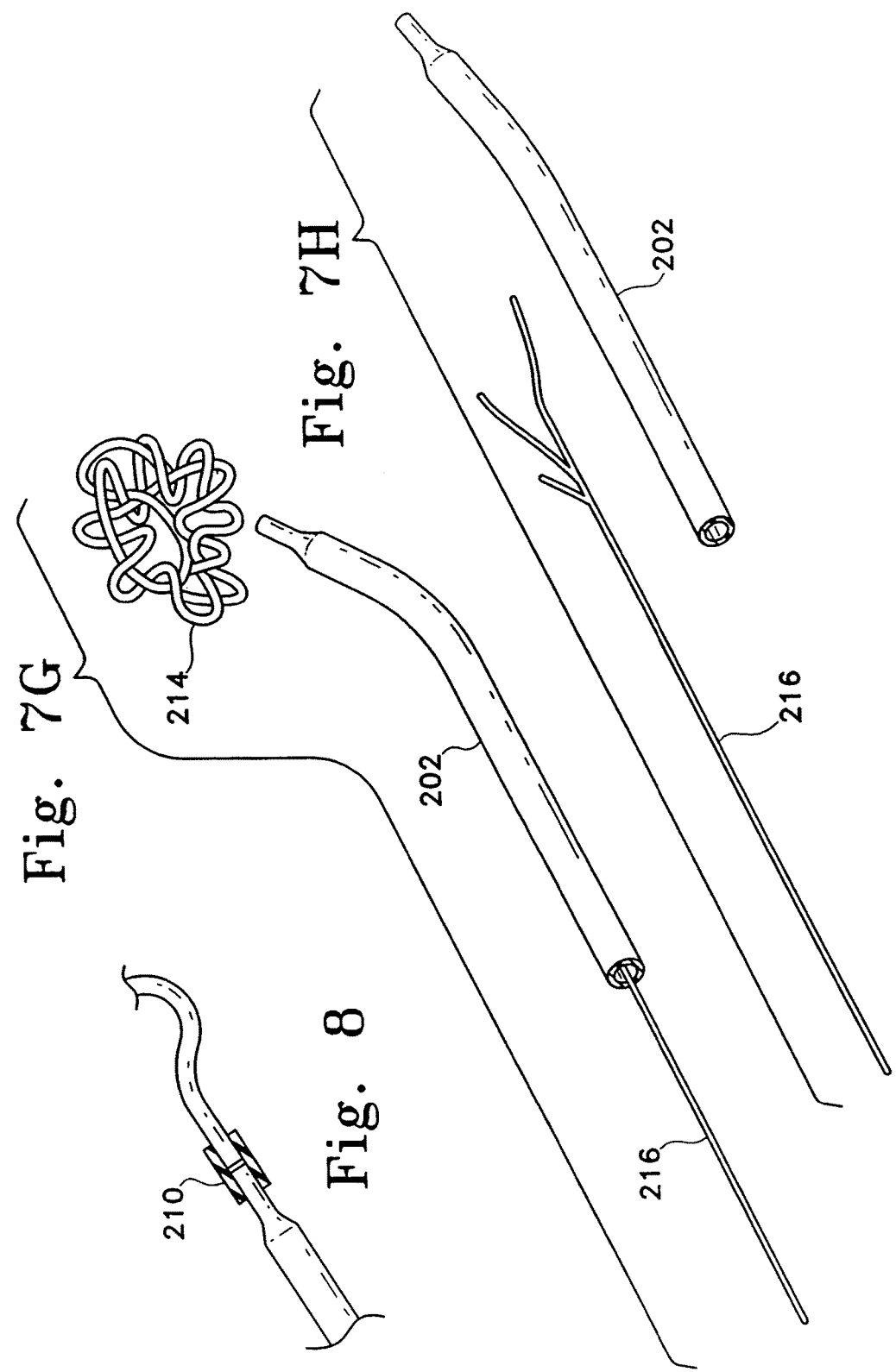

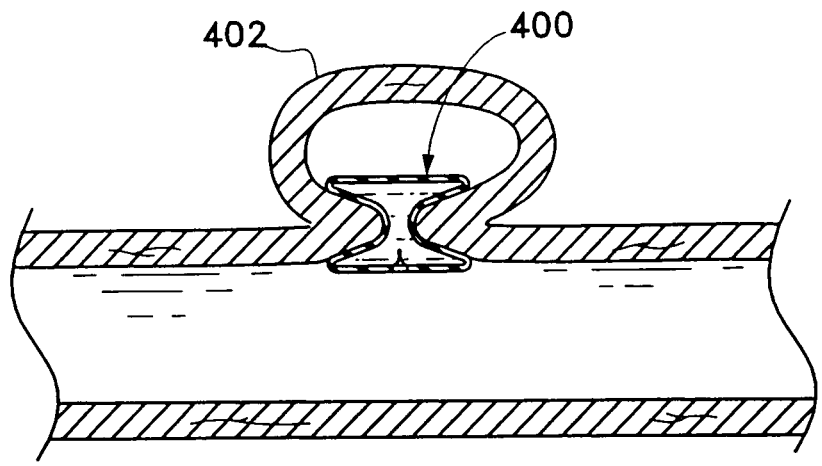
Fig. 10A
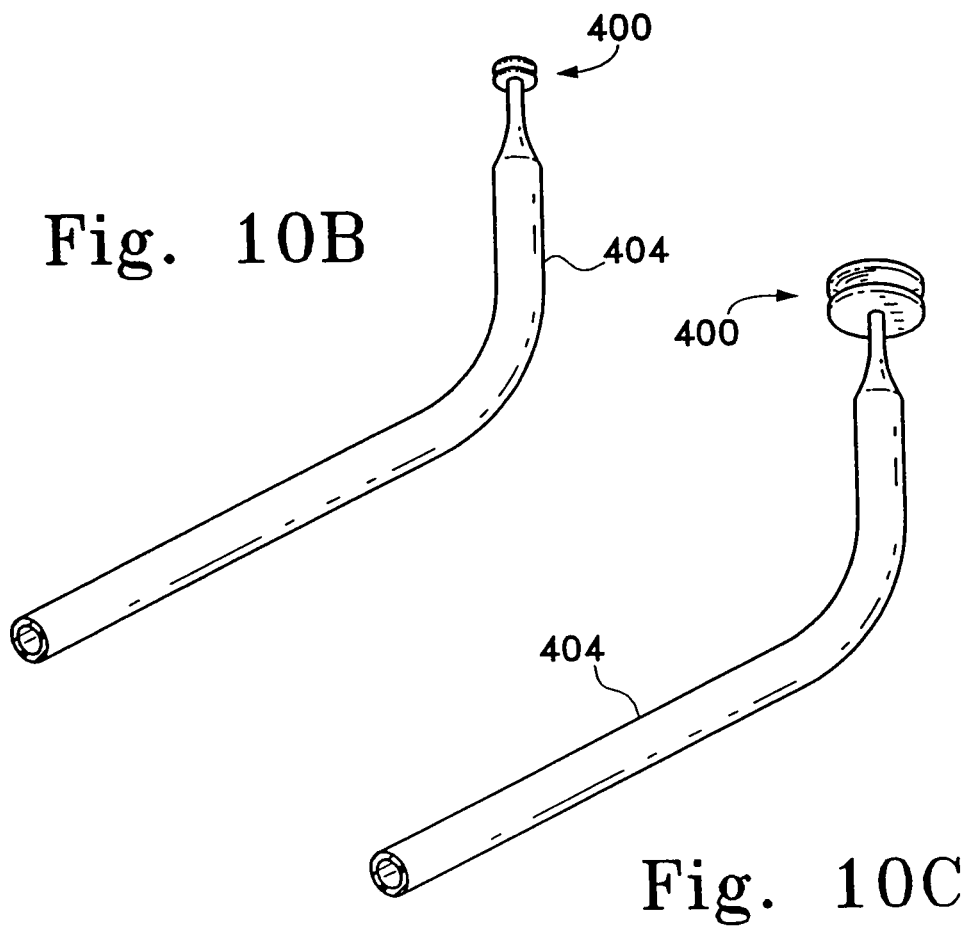
Fig. 10B
Fig. 10C

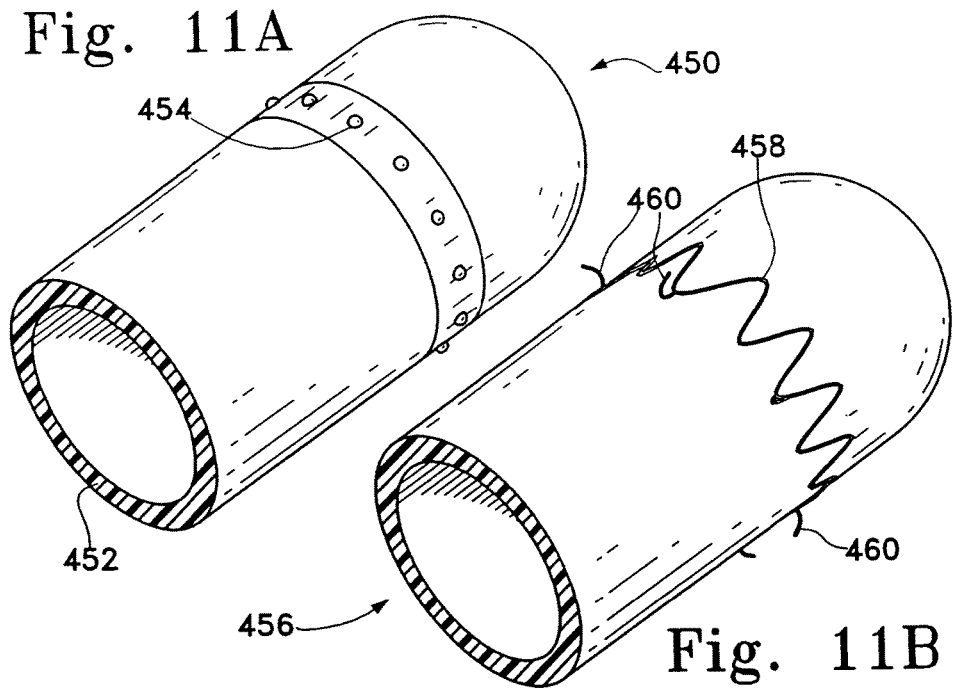
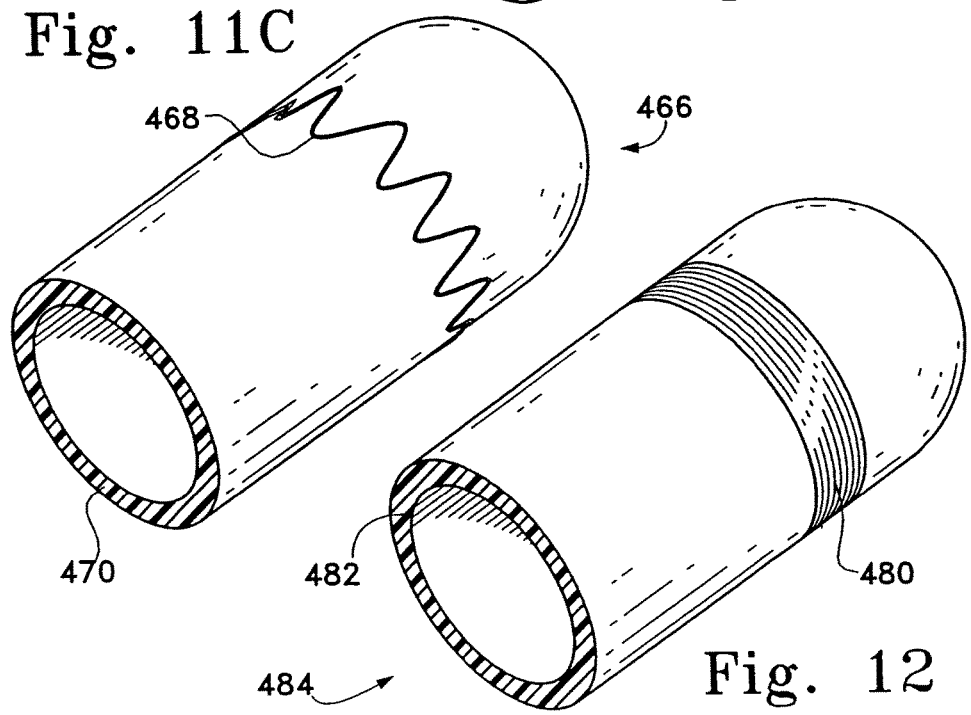

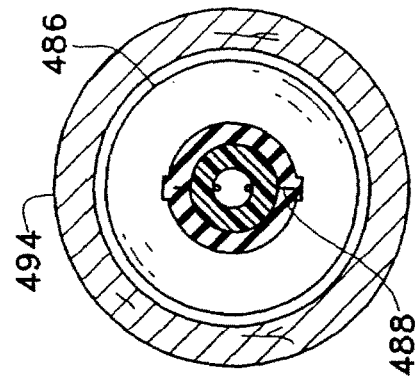
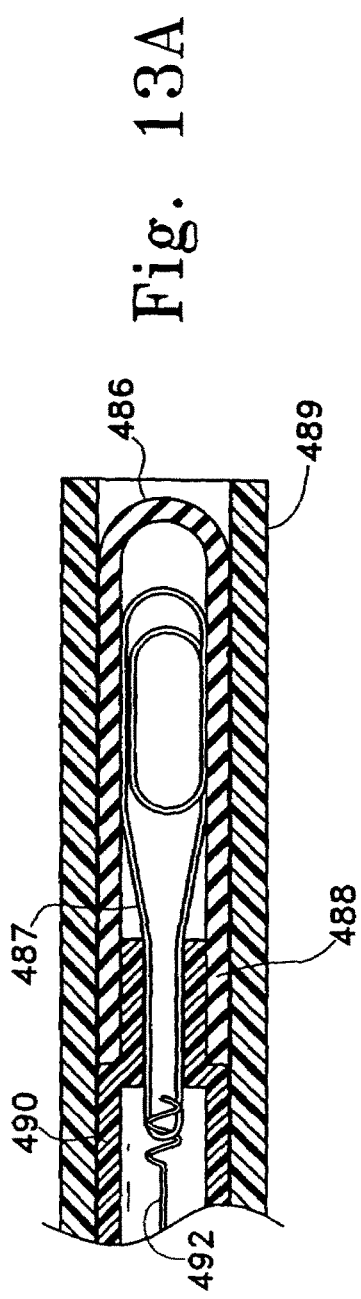
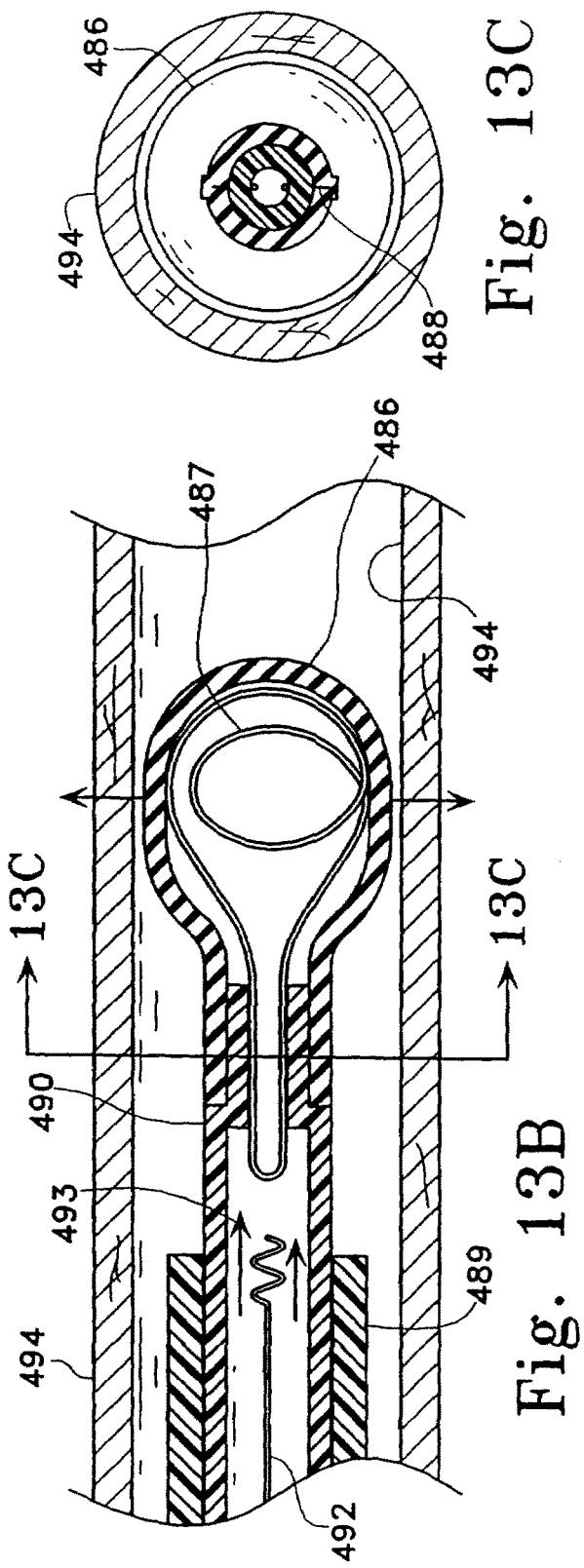

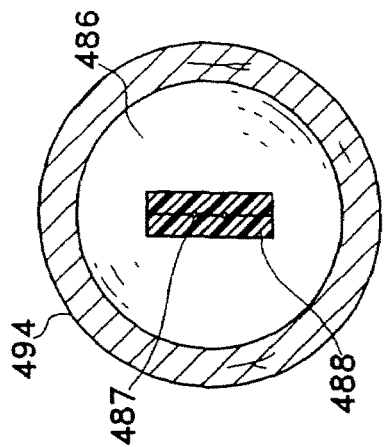
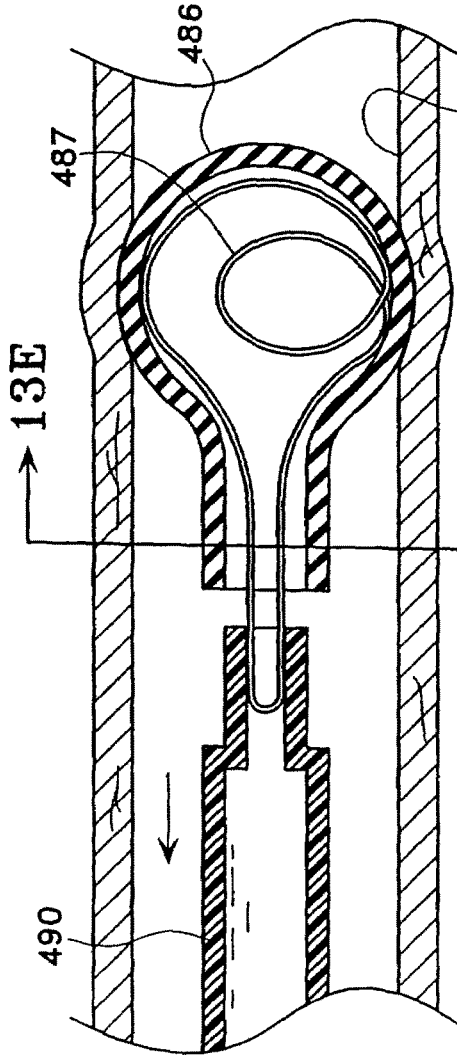
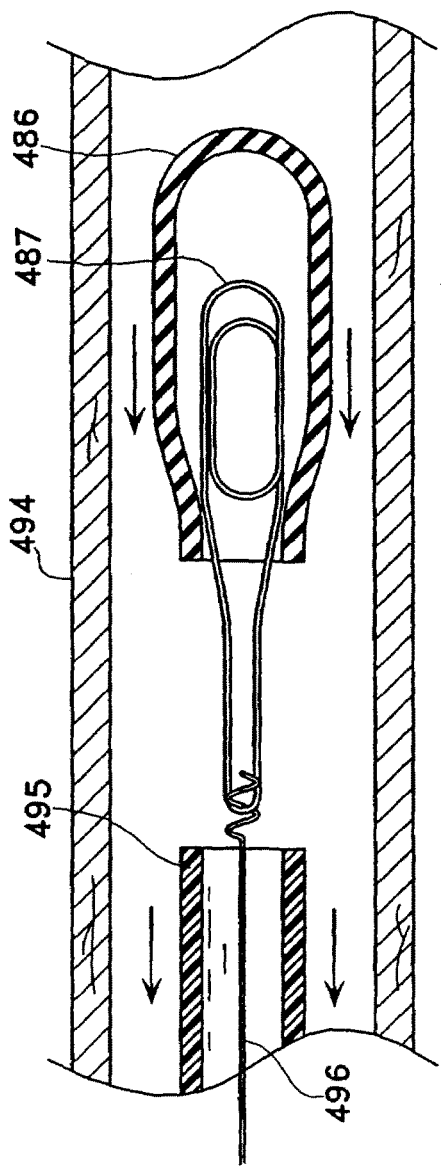

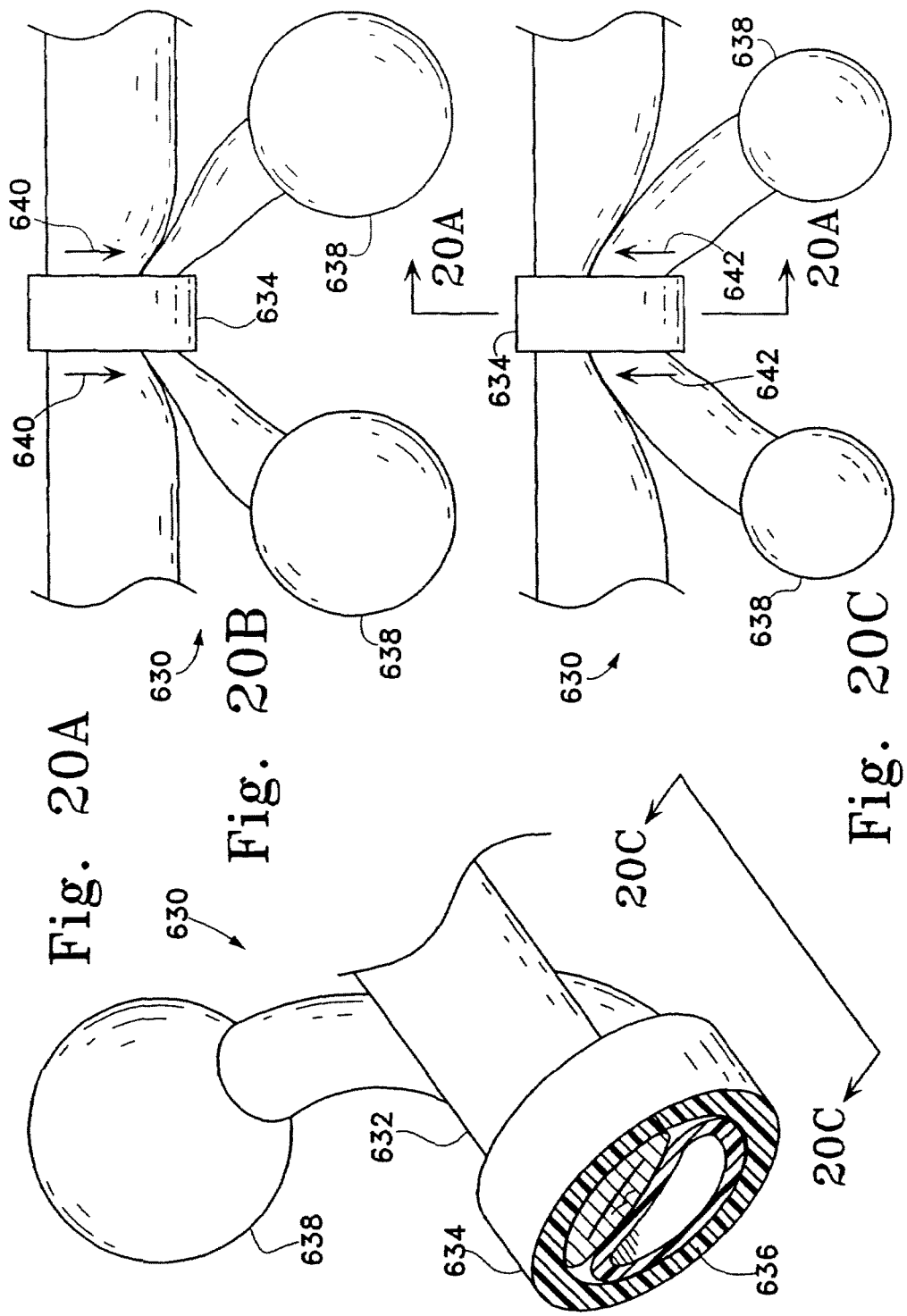

INFLATABLE IMPLANT

CROSS-REFERENCE TO RELATED APPLICATIONS

This application is a Division of U.S. application Ser. No. 10/461,853 filed on Jun. 13, 2009 the entire contents of which are incorporated by reference herein.

FIELD OF THE INVENTION

This invention is in the field of surgery. In general, it is an inflatable implant suitable for placement in the human body and left there for an indeterminate and potentially lengthy period of time. The implant is one that has a low profile when introduced into the body and a larger profile when it is inflated with one or more filler materials. Depending upon design and use choices the delivered implant may be removable and adjustable in situ in size, position, location, form, and rigidity. Indeed, in some variations, the design of the implant may be such that it may be removed at a potentially fairly lengthy time after implantation. The implant includes at least one bladder wall that generally is at least partially non-elastic (or unexpandable) after the preselected size is reached. The bladder wall (or walls) will define at least one fillable volume and may form more than one independent fillable volumes. The bladder wall, in some variations, may be partially elastic or expandable to permit adjustment of implant size or configuration after or during delivery. The implant may be used as a supporting structure in a variety of differing body tissues and structures, e.g., in the spine or as a prosthetic in plastic surgery. The implant may also be used in conjunction with other components (often having a springed bias) as a source of movement in controlling the opening of a lumen or duct, that is to say, as a type of on-off valve or as a controlled flow valve. The implant may be used as an occludant within, or adjacent to, a variety of natural or abnormal anatomical body openings, e.g., vascular and genital lumina, aneurysms, ducts, septal defects, fistulae, esophagus, etc. The wall and filler material may be selected to deliver treatment materials to the locale of the implant site or to remove amounts of harmful materials from such a region. The implant may, with an appropriate filler material or bladder wall material, be used in cooperation with an appropriate radio frequency (RF) source to cause the increase of a localized internal temperature and a resulting tissue change such as coagulation, ablation, or the like. Methods of using the implant are also described.

BACKGROUND OF THE INVENTION

Described is an inflatable, expandable implant suitable for implantation in a human body. In general, it is a device that may be implanted in the body at a placement site in a lower profile form and expanded after placement. The implant may be used, for instance, to occlude or to support some region of the body.

The described implant may have a bladder with a substantially non-elastic bladder wall that defines a volume, and at least one bladder wall opening for introduction of filler material. In some examples of the implant, the bladder will have no passageway exterior to the bladder wall for passage of a body fluid from an end of the bladder to the other end. The bladder may have at least one closure for each of the at least one bladder wall openings. The closures operate to maintain the filler material within the bladder after its introduction. If the filler material is selected to be of the type that reacts in the bladder to form a non-flowing mass, a closure may not be necessary.

The use of occluding materials or implants over the past few years to occlude various areas in the body has expanded. For instance, in treating many vascular problems, the artificial blocking of blood flow, known generically as "embolization," is used. The embolization of a blood vessel in an organ may be used to treat a variety of maladies; typically, though, embolization is used: 1) to control the bleeding caused by trauma, 2) to prevent profuse blood loss during an operation requiring dissection of blood vessels, 3) to obliterate a portion of or a whole organ having a tumor, or 4) to block the blood flow into abnormal blood vessel structures such as arterio-venous malformations (AVM's) and aneurysms. For such treatments, a variety of mechanical and chemical occludants are available. Such occluding materials include platinum and stainless steel microcoils. Platinum microcoils sold as Guglielmi Detachable Coils (GDC) by Boston Scientific Corporation are effective in many instances. However, significant skill is required to choose a coil size proper for the malady prior to delivery. Many anatomical sites are not suitable for use of microcoils, and removal is difficult.

Other occludants include polyvinyl alcohol sponges (Ivalone) and cyanoacrylate glues (n-butyl and iso-butyl cyanoacrylates). Of these, the cyanoacrylate glues have an advantage over other embolic materials in ease of delivery in that they are the only liquid embolics currently available to physicians. However, the constituent cyanoacrylate polymers have the disadvantage of being biodegradable. The degradation product, formaldehyde, is highly toxic to the neighboring tissues. See Vinters et al, "The Histotoxocity of Cyanoacrylate: a Selective Review", Neuroradiology 1985; 27:279-291. Another disadvantage of cyanoacrylate materials is that the polymer will adhere both to the blood vessel and to the tip of the catheter. Thus physicians must retract the catheter immediately after injection of the cyanoacrylate embolic material or risk adhesion of the cyanoacrylate and the catheter to the vessel. Removal and choice of occludant size are major problems.

Another class of liquid embolic materials, precipitative materials, was invented in late 1980's. See Sugawara et al, "Experimental investigations concerning a new liquid embolization method: Combined administration of ethanol-estrogen and polyvinyl acetate", Neuro Med Chir (Tokyo) 1993; 33:71-76; Taki et al, "A new liquid material for embolization of arterio-venous malformations", AJNR 1990:11:163-168; Mandai et al, "Direct Thrombosis of aneurysms with cellulose acetate polymer. Part I: Results of thrombosis in experimental aneurysms." J. Neurosurgery 1992; 77:497-500. These materials employ a different mechanism in forming synthetic emboli than do the cyanoacrylate glues. Cyanoacrylate glues are monomeric and rapidly polymerize upon contact with blood. Precipitative materials, on the other hand, are pre-polymerized chains that precipitate into an aggregate upon contact with blood.

In the precipitation method, the polymer is dissolved in a solvent that is miscible with blood, and upon contact with that blood, the solvent is diluted and the water-insoluble polymer precipitates. Ideally, the precipitate forms a solid mass and thus occludes the vessel.

The first such precipitative material used in this way was polyvinyl acetate (PVAc). Also, poly(ethylene-co-vinyl alcohol) (EVAL) and cellulose acetate (CA) dissolved in 100% dimethyl sulfoxide (DMSO) have also been used in clinical procedures. See Taki et al, "A new liquid material for embolization of arteriovenous malformations", AJNR 1990; 11:163-168 and Mandai et al, "Direct thrombosis of aneurysms with cellulose polymer: Part I: Results of thrombosis in experimental aneurysms", J. Neurosurgery 1992; 77:497-500. Partially hydrolyzed polyvinyl acetate in, e.g., ethanol, is also an available member of this class.

Each of these precipitative materials shares potential use problems in that: (1) they introduce organic solvents into the body, materials that can damage microcapillary vessels and surrounding tissues and are also known to cause vasospasm of blood vessels, and (2) placement of a precipitating polymer and estimation of the resulting precipitated mass is, at best, an inexact science.

The filled bladder implant described herein does not share any of these problems when used as an occluding device, may placed with better precision, and (when designed to do so) may be removed from the implantation site.

SUMMARY OF THE INVENTION

Described is an inflatable, expandable implant suitable for implantation in a human body. In general, it is a device that may be implanted in the body at a placement site in a lower profile form and expanded after placement. The implant may be used to occlude fill or support some region of the body.

The described implant may, in many examples of the implant, have a bladder with a substantially non-elastic bladder wall that defines a volume, at least one bladder wall opening for introduction of filler material. In many other examples of the implant, a bladder having an elastic bladder wall may be present. In some examples of the implant, the bladder will have no passageway exterior to the bladder wall for passage of a body fluid from an end of the bladder to the other end. The bladder may have at least one closure for each of the at least one bladder wall openings. The closures operate to maintain the filler material within the bladder after its introduction. If the filler material is selected to be of the type that reacts in the bladder to form a non-flowing mass, a closure may not be necessary.

The implant may be configured to achieve many results in a human body. For instance, the implant may be given a form that at least partially closes a body opening (and perhaps allows reopening of that lumen), e.g., a lumen such as a vascular lumen, genito-urinary lumen, bronchial lumen, gastrointestinal (G-I) lumen, or hepatic lumen, in a human body by placement or implantation in that body opening. This closing and opening may, depending upon the design, be controlled by the patient or by the physician. It may be of a type that simply provides additional closing force to a leaky fluid pathway but still allow the patient to use their own muscle tone to perform the step of opening the lumen.

The implant may, depending upon the design, be placed around, adjacent to, or within the lumen. The implant may be placed as desired in a region where additional bulk is needed (e.g., in reconstructive surgery) or where some support is needed (e.g., in a joint such as the knee, spine, elbow, or wrist). The implant may take the form of a plurality of hollow fibers or may have multiple chambers or may have a number of different wall materials, perhaps some elastic some not or all of one or the other. Each chamber may have a separate filler and closure as needed.

The implant may be designed to be removed at a later time. For instance, the implant may include a retrieving member, adapted to cooperate with a retriever, allowing removal of the implant from the body particularly by access of the retriever through the body lumen and removal through that body lumen. The retrieving member may be an integral portion of the implant, that is to say that it is not separable from the implant once deployed, or it may be movable with respect to the rest of the implant.

The described implant may comprise the filler material. The filler material may be a liquid, solid, gas, or other suitable form. It may be of a type that reacts to form a solid or gel in implant after implantation. The filler material may be a filling liquid, perhaps selected from the group consisting of water, saline, and biocompatible liquids. It generally is to be flowable at implantation.

The filler material may contain a wide variety of ancillary materials. For instance, it may contain one or more radiopaque material, fluids such as those selected from the group consisting of iopromide, metrizamide, and their mixtures and solutions, and solids such as barium sulfate, bismuth trioxide, and bismuth carbonate, and metals such as tungsten, tantalum, gold, ruthenium, rhodium, osmium, iridium, palladium, platinum, rhenium, and their mixtures. The filler material may contain materials that absorb radio frequency energy. Such radio frequency energy absorbing materials may be selected from the group consisting of iron oxides, iron hydroxides, graphite, and amorphous carbon. Other ancillary materials are radioactive, bioactive, or chemi-active.

One desirable class of filler materials is a reactive mixture that reacts within the bladder volume, such as, elastic solids, viscoelastic solids, viscoelastic liquids, viscoelastic liquids comprising gel microparticles, viscous liquids, and their precursors. In particular, such materials comprise copolymers of a first member selected from the group consisting of poly(ethylene glycol), poly(ethylene oxide), poly(vinyl alcohol), poly(ethylene-co-vinyl alcohol), poly(acrylic acid), poly(ethylene-co-acrylic acid), poly(ethyloxazoline), poly(vinyl pyrrolidone), poly(ethylene-co-vinyl pyrrolidone), poly(maleic acid), poly(ethylene-co-maleic acid), poly(acrylamide), and poly(ethylene oxide)-co-poly(propylene oxide) block copolymers and a second member having a strong nucleophile selected from the group consisting of a thiol or a group containing a thiol.

Complementary mechanical ancillaries include one or more anchors configured to maintain the implant in a selected position in the human body after introduction of a filler into the volume. They may be in the form of at least one anchoring region exterior to the bladder wall and configured to maintain the implant in a selected position in the human body after implantation, perhaps fixed to the bladder wall. Often such an anchor, for example, a stent, is self-expanding upon deployment. Another mechanical ancillary includes at least one forming member situated within the bladder volume and it is used to form a deployed bladder wall shape upon deployment. The forming member may variously be included in a form that is not to be removed after deployment, that is to be removed after deployment, or that is used in another function or two, e.g., to deflate the bladder or act as a catcher for a manipulable retriever to allow removal of an implant.

The bladder wall may be of a variety of materials, woven fabrics and non-woven fabrics, perhaps of polymers such as at least one member selected from the group consisting of polyethyleneterephthalate, polyvinylchloride, polyurethanes, polyolefins, polyamides, and fluoropolymers, perhaps at least one fluoropolymer selected from the group consisting of polytetrafluoroethylene, poly(ethylene-chlorofluoroethylene), poly (fluorinated ethylene propylene), polychlorotrifluoroethylene, polyperfluoroalkoxy, polyvinylfluoride, polyvinylidenefluoride, and expanded polytetrafluoroethylene (ePTFE). The material ePTFE is quite useful. The bladder wall may also include materials such as carbon fiber, metal fiber, and alloy fiber where the task needs.

When the implant is used to heat a localized region within the body, at least one of the bladder wall and the filler material comprises a radio frequency energy absorbing material such as iron oxides, iron hydroxides, graphite, and amorphous carbon. Again the filler material may contain radiopaque material such as those discussed above.

One use for the implant is as a "valving assembly" used to control the flow of body fluids through a body tubular member lumen. The assembly may be of a number of designs depending, e.g., upon the lumen to be controlled. One such design, where the body lumen is normally closed (for instance, the urethra), closes the lumen, but can be adjusted or sized to permit the patient to use their own muscles to open the lumen against the added implant pressure. Such an assembly might be made up of an implant member comprising an inflatable, expandable bladder with a substantially non-elastic bladder wall defining a volume, having at least one bladder wall opening for introduction of filler material, and at least one closure for each of the at least one bladder wall openings. Additionally, the implant might include a housing member having an open interior, and a spring member (e.g., a bladder or spring). This example of the implant is installed around the lumen in such a way that the spring member is biased to close the body lumen by pressing the body tubular member against the implant member. The implant member is inflatable with filler material to an amount allowing the lumen, in cooperation with the spring member, to open upon introduction of body fluid pressure in the lumen (by the patient) and to close upon release of the pressure.

The valving assembly may include the filler materials and the ancillary materials discussed elsewhere herein.

Another valving assembly for controlling the flow of body fluids in a lumen in a body tubular member may use a housing member having an open interior and an implant member comprising an inflatable, expandable bladder that is at least partially elastic and having a bladder wall as the controlling surface to close the lumen against the housing member. The overall elasticity of the bladder is adjustable upon implantation by filling with a filler material in an amount appropriate to press the lumen closed against the housing member and to permit the lumen to open upon introduction of body fluid pressure in the lumen and to close upon release of the pressure. In another example of this variation, the implant member is configured to allow movement of filler material into a partially elastic portion of the bladder during the introduction of body fluid pressure in the lumen.

A specifically controllable example of such a device is one in which the implant member includes an inflatable, expandable bladder having a substantially non-elastic bladder wall defining a volume, having at least one motive section and a palpation reservoir hydraulically connected to, but remote from, that at least one motive section. When the palpation reservoir is squeezed, the motive section expands to move the spring member, and to allow the lumen to open.

BRIEF DESCRIPTION OF THE DRAWINGS

FIG. 2A shows a side view of another variation of the implant, as collapsed for delivery.

FIG. 2B shows a side view of the implant of FIG. 2A after inflation.

FIG. 3A shows an end view of a substantially round implant.

FIG. 3B shows the implant of FIG. 3A in a side view.

FIG. 4A shows an end view of a long, tubular implant.

FIG. 4B shows a side view of the implant of FIG. 4A.

FIGS. 7A, 7B, 7C, and 7D show, respectively: a deflated implant having fillable hollow fibers as delivered to a treatment site, that device after inflation, and that implant after release.

FIGS. 7E, 7F, 7G, and 7H show, respectively: a deflated implant having fillable hollow fibers as delivered to a treatment site similar to that shown in FIG. 7A but having a complex batten, that device after inflation, that implant after release, and the delivery device and the batten after removal from the implant, in the instance that the batten is removed.

FIG. 8 shows the inflation end of the implant shown in FIGS. 7A, 7B, and 7C.

FIGS. 10A, 10B, and 10C show, respectively, the placement of a plug-like, occlusive implant situated in an aneurysm mouth or throat, the implant ready to be delivered into the body, and the implant after inflation.

FIGS. 11A, 11B, and 11C show various components for fixating or immobilizing the implant using respectively nubs, hooks, and a stent.

FIG. 12 shows the placement of a radiopaque band upon the implant.

FIGS. 13A, 13B, 13D, and 13F show longitudinal, sectional views of an implant that may be retrieved after delivery and the sequence involved in placement and in retrieval. FIGS. 13C and 13E are cross sectional views of FIGS. 13B and 13D, respectively.

FIGS. 20A, 20B, and 20C show a valving assembly utilizing an implant having one or more partially elastic sections that may be used in controlling or stopping flow through a human body lumen.

DESCRIPTION

Figure 1A:
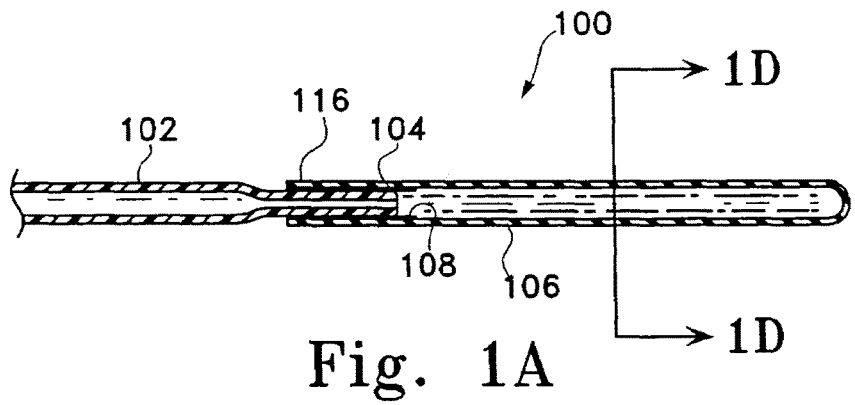
FIG. 1A shows a side, partial cutaway of a variation of our implant, collapsed and ready for introduction into the body.
Figure 1B:
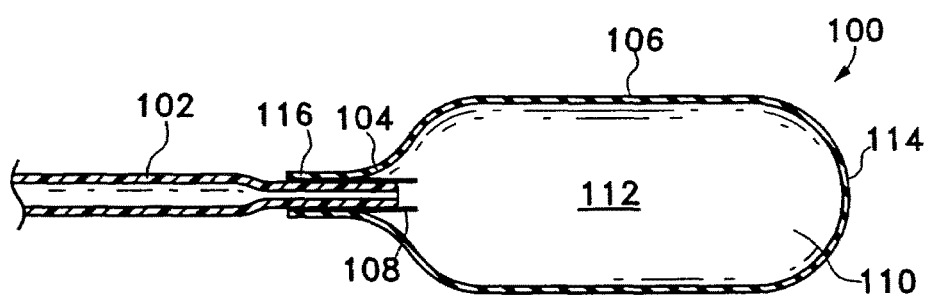
FIG. 1B shows a side, partial cutaway of the implant of FIG. 1A after inflation of the bladder with a filler material.
Figure 1D:
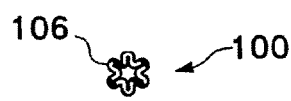
FIG. 1D shows a cross section of the implant shown in FIG. 1A.
Figure 1C:
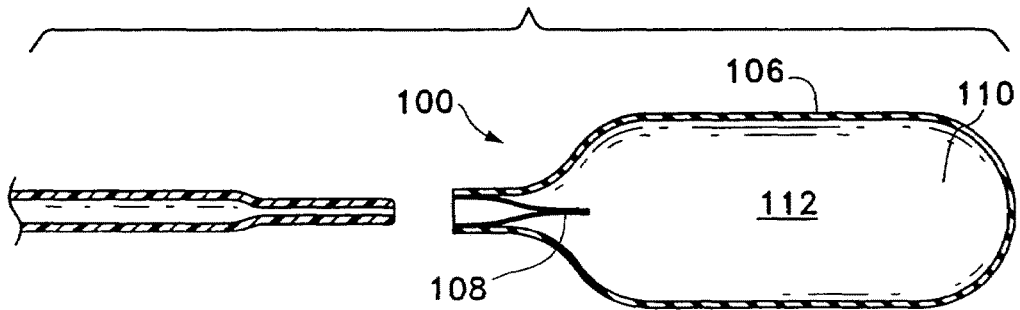
FIG. 1C shows the implant of FIGS. 1A and 1B after release of the implant from the feed catheter.

FIGS. 1A, 1B, 1C and 1D show a typical implant made according to this description, its major constituent parts, and (with the three Figures taken together) show one way of utilizing the implant. FIG. 1A shows the folded and pleated implant bladder (100) and its associated filler device (102), e.g., a catheter, the opening (104) through bladder wall (106), and a closure or valve (108) situated, in this variation, in the opening (104) through bladder wall (106). The closure (108), in this instance, is a "duck bill" one-way valving mechanism that holds a flowable filler within the bladder (100) once it is inflated as shown in FIGS. 1B and 1C. To the right of in FIG. 1A is a cross-sectional view of bladder (100) ready for implantation, showing the folding of the bladder wall (106) in a lobed configuration. Folding a fillable bladder in this way allows the user to introduce the implant into fairly small places and allows arrival of the implant and ease of placement in a fair hurry. In many instances when using platinum coils and the like as occlusive devices, the length of the coils to be delivered is substantial. In some instances, many linear feet of coils must be pushed through a catheter lumen to the site to be occluded. Occasionally, the length calculation is inaccurate. The coil may then be delivered before the realization is had that the length of the coil is too long for the volume to be occluded which leads to a remainder of the coil extending into, e.g., the adjacent patent vessel. This implant allows in situ adjustment of the occludant size by controlling the amount of introduced filler material.

FIG. 1B shows the bladder (100) after it has been inflated by filler material (110). Filler material (110) expands the bladder wall (106) to a specific pre-chosen shape, past which the bladder (100) will expand no further. Bladder wall (106), in this example of the invention, includes a continuous non-elastic bladder wall (106) which in turn defines a volume (112) into which the filler material is pushed. In FIG. 1B, the filler device (102) is shown to be inserted into the opening (104) in bladder wall (106) and the closure (108) is shown to be open as well.

It should be noted that unlike the endovascular grafts shown in U.S. Pat. No. 6,395,019, to Chobotov, the entirety of which patent is incorporated by reference, the implant of FIG. 1 and the others described herein, have no central passageway allowing passage of body fluid between its distal end (114) and its proximal end (116). Other embodiments of the present invention, however, may have such a central passageway or similar conduit arranged in a different configuration as is explained in detail below.

FIG. 1C shows, in side view cross-section, the implant made up of the bladder (100), the bladder wall (106), filler material (110) occupying bladder volume (112), and the closure (108) with its bills closed to maintain the filler material (110) within volume (112) now that the bladder (100) has been inflated.

The materials of construction for various of these components are described below in greater detail.

FIGS. 2A through 5B are examples of the wide variety of shapes into which the implant may be made. FIG. 2A shows an implant (140) having a folded a collapsed bladder (142) and filler introduction component (144) inserted into bladder (142). Bladder (142), as collapsed, may be quite small in diameter and length. FIG. 2B shows a side view of the implant (140) in which the bladder (142) has been expanded into a large disk-like shape. Such a shape might be useful in treating an arterio-venous malformation.

FIG. 3A shows an end view of an additional example of a bladder implant (144). FIG. 3B, similarly, shows a side view of that substantially round, inflated bladder (146).

FIG. 4A shows an end view of a bladder (148) having a substantially round section. FIG. 4B shows, in side view, the tubular shape (150) of the bladder wall (150).

Figure 5A:
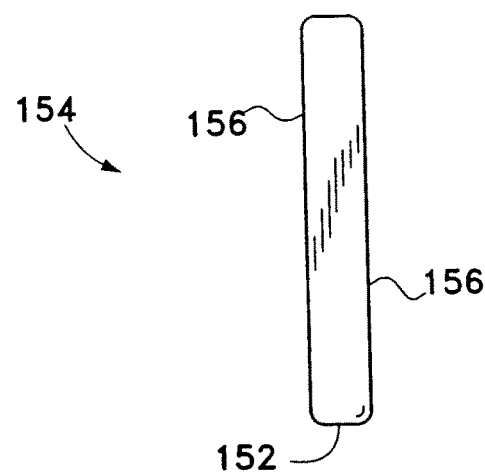
FIG. 5A shows an end view of a flat, panel-like implant.
Figure 5B:
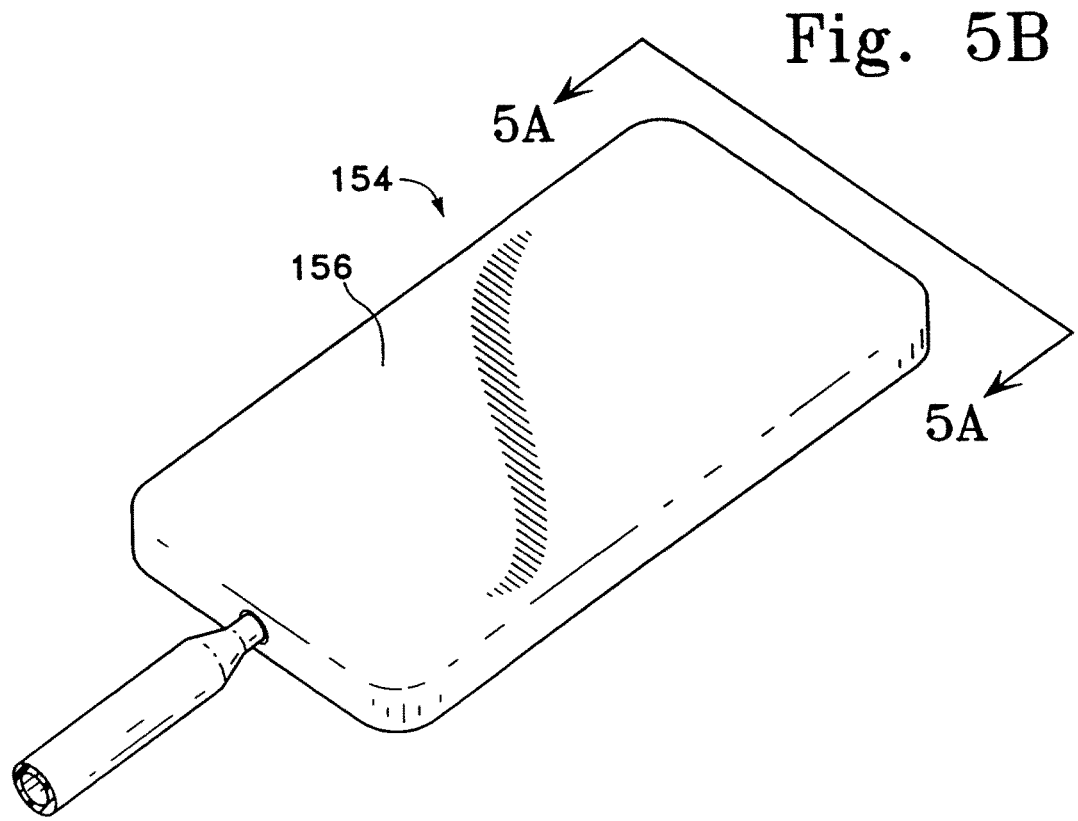
FIG. 5B shows the implant of FIG. 5A in perspective view.

FIG. 5A provides an end view of bladder wall (152) and FIG. 5B shows a perspective view of that device (154). The implant (154) shown in FIGS. 5A and 5B is generally flat, perhaps with the larger surfaces (156) ballooning a bit. An implant such as shown in FIGS. 5A and 5B might be used in plastic or reconstructive surgery in supplementing soft tissue shape, for instance, in re-shaping a chin or cheek.

Additionally, an implant having a shape such as that of implant (154) and designed to ultimately be removable from the body, may be placed beneath a region of skin where the skin later is to be harvested for, e.g., burn treatment on a section of the body. The skin situated over such site is thereby expanded, increasing the available area of skin for that later removal.

Figure 5C:
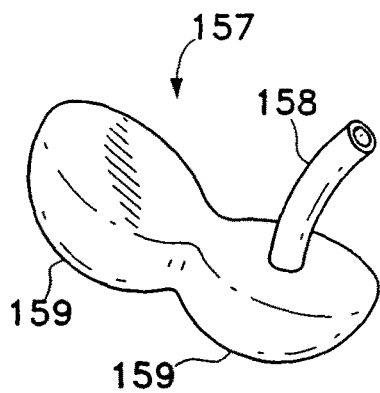
FIG. 5C shows a perspective view of an implant suitable for augmentation of soft tissue, e.g., the tissue in the chin.

FIG. 5C shows a perspective view of a chin implant (157) having lobes that expand upon inflation through inflation member (158). A design choice is to be made here relating to the filler material used and therefore whether a sealing valve of some type is needed in filling member (158). Since a chin implant may be soft to the touch, it may be desirable to use a filling medium that does not polymerize (such as the triglycerides of various saturated and unsaturated carboxylic acids or edible oils such as vegetable or nut oils) or one that polymerizes to a gel-like consistency. In either case, some accommodation for holding the filling medium in the volume defined by the bladder wall of chin implant (157) must be had. A one-way valve, perhaps of the design shown elsewhere herein, is one choice. A clamp on the filling member (158) is similarly acceptable. If a polymerizable filler is used, a valving member might not be suitable. Similar considerations relating to the filling devices are to be made for each of the devices disclosed here.

Figure 5D:
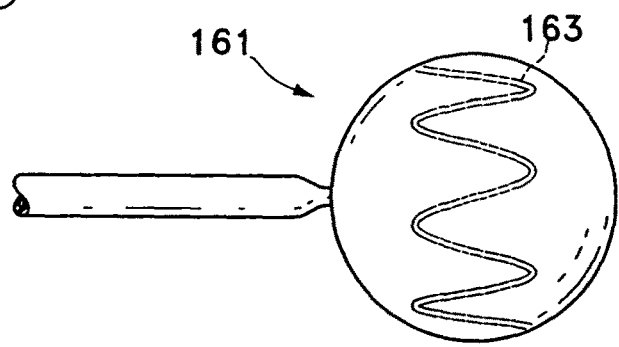
FIG. 5D shows a perspective view of an implant having a support member in the bladder wall.

FIG. 5D shows an implant (161) similar in form to that shown in FIGS. 3A and 3B. This Figure depicts a stabilizing element (163) situated in the bladder wall. The stabilizing element (163) depicted is a simple zigzag wire comprising, e.g., a superelastic alloy such as nitinol or a stainless steel, and is intended to provide a measure of shape stability during either, or both of, deployment or after final deployment. A variety of such stabilizing elements coupled to the bladder wall for this variation and others described here are acceptable for various uses—braids, wires, ribbons, random fibers, woven fibers, etc. depending upon the use to which the implant is placed.

Figure 6:
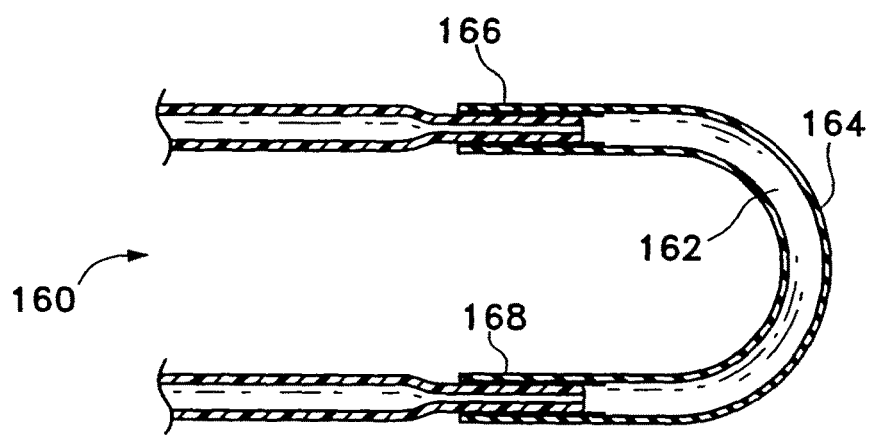
FIG. 6 shows a partial cross-section of a horseshoe-shaped implant with dual filler material entrances.

FIG. 6 shows still another example of the implant (160). In this variation, the implant bladder wall (164) includes two passageways, respectively (166) and (168), and closures or valves associated with each passageway. These openings (166, 168), of course, open into bladder volume (162). The implant (162), in this example, is semi-circular. Of course, the overall shape of implant (162) may be of any convenient arc size, depending upon the service into which it is placed. That is to say that the shape of implant (160) is not limited to a mere semi-circle, but instead may be any portion of a circle or, if such is needed, more than a 360° loop with some overlap at the ends or even of a design that will follow any convenient curve. The cross-sectional shape may be elliptical or partially elliptical or oval or partially oval, indeed, any shape amenable to the introduction of a filler material into the bladder volume (162). The example shown in FIG. 6 is for the purpose of explaining and describing a variation in which more than one entrance to the bladder volume is used and further describes a variation of the implant in which a chosen bladder conformation is narrow at some point in the interior volume. Flow problems potentially associated with such a narrow bladder configuration may be alleviated by introduction of a filler material to more than one point. Such a solution may also appropriate where the filler is viscoelastic or is some type of a non-Newtonian fluid. Additionally, depending, again, upon the service into which the device is place, the medical treatment may require inflation of one part of the bladder prior to inflation of another. For instance, use of a partially circular, oval, or semi-circular bladder in replacement of or stabilization of a cervical disk might require introduction of filler from one specific end of the bladder.

An implant (160) having a structure such as shown in FIG. 6 may be used to replace intervertebral disks or to augment herniated or degenerated disks. Similarly, such an implant may be used to provide added "firming" structure to or to replace various bursa in and around the knee and elbow.

FIGS. 7A, 7B, 7C and 7D show a variation of the implant that utilizes a number of fairly small tubular members as the bladder wall. The resulting, inflated implant resembles a small fibrous ball or construct that might, for instance, be used to occlude a vascular aneurysm. Because of its shape and very high surface area compared to its volume, it may also be suitable for delivery of medication or the like to the surrounding region. One such instance would include construction of the implant of a size adequate to remain in the human bladder after placement, having a medication in the filler material that is permeable through the bladder wall. Depending upon the filler and bladder wall material chosen, the implant may be designed to be "self-passing" after the medication is depleted or be designed to be retrieved after depletion.

FIG. 7A shows a portion of a delivery device (200) with, e.g., a delivery catheter (202), having the implant (204) in a collapsed condition mounted at its distal extremity ready for delivery. Not shown, simply because of the size of the drawing, is the opening into the multi-hollow-fibered bladder wall (206).

FIG. 7B shows the expanded implant (204) and FIG. 7C the details of bladder wall (206) in the blown up portion of the implant shown in FIG. 7B.

FIG. 7D depicts the implant (204) after separation from the filler feed device (202).

As noted above, occluding devices of the shape shown in FIGS. 7A, 7B, and 7C, and 7D are very useful in occluding saccular aneurysms. There are a number of commercially available platinum-coil-based products that are delivered through endovascular catheters specifically for the purposes of: filling of such aneurysms, forming of a clot to occlude the aneurysm, and therefore preventing the aneurysm from rupturing or leaking with subsequent, perhaps catastrophic, results. When used in an aneurysm, our described implant is significantly easier to deliver in a size that is suitable for that aneurysm. That is to say, it is often difficult determine the length of platinum coil needed for proper occlusion of the aneurysm. But, the use of our described implant allows the user to fill the implant only so much as is needed to inflate the implant to a suitable size, all while observing (e.g., by fluoroscopy or ultrasound or by other non- or minimally-invasive procedure) the size of the implant device during that filling step. Because our implant device may include thrombogenic materials on its surface and consequently available to the blood in the aneurysm, the device may provide a quicker resolution of an aneurysm than various other known devices and procedures.

Figure 9A:
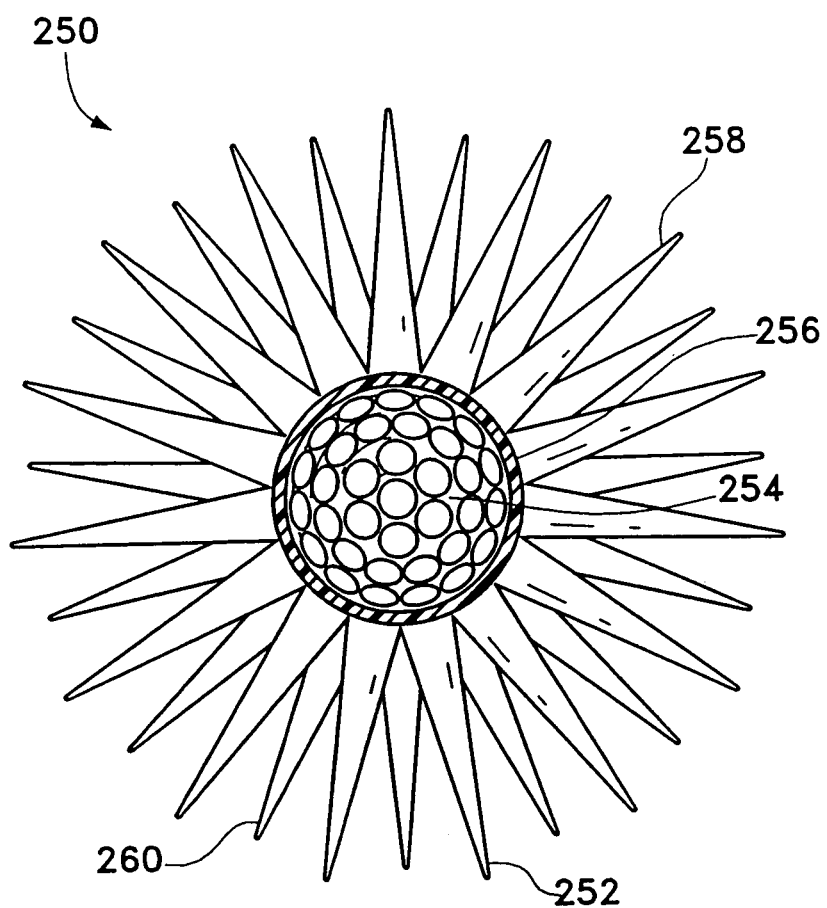
FIG. 9A shows an example of the implant shaped much like a sea urchin.
Figure 9B:
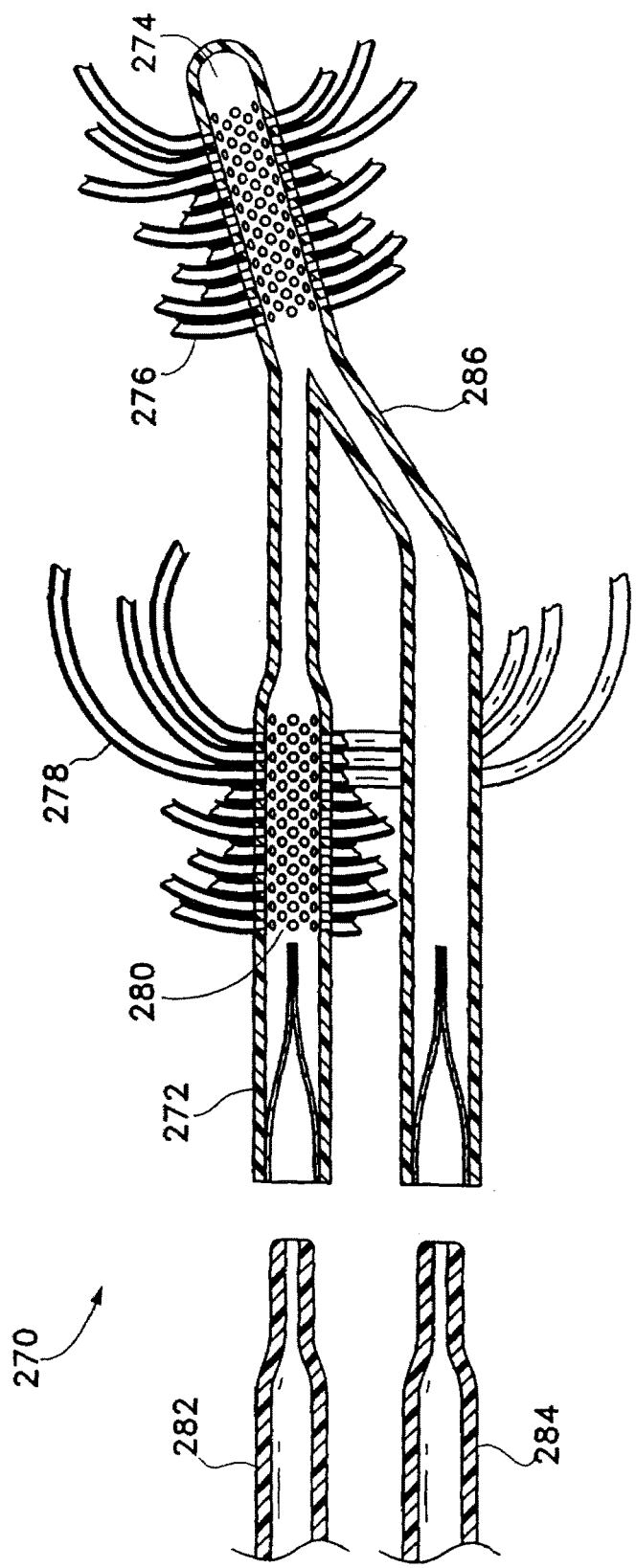
FIG. 9B shows a variation of the implant having dual inflation entrances for filler materials and using hollow fibrous sections in the bladder wall.
Figure 9C:
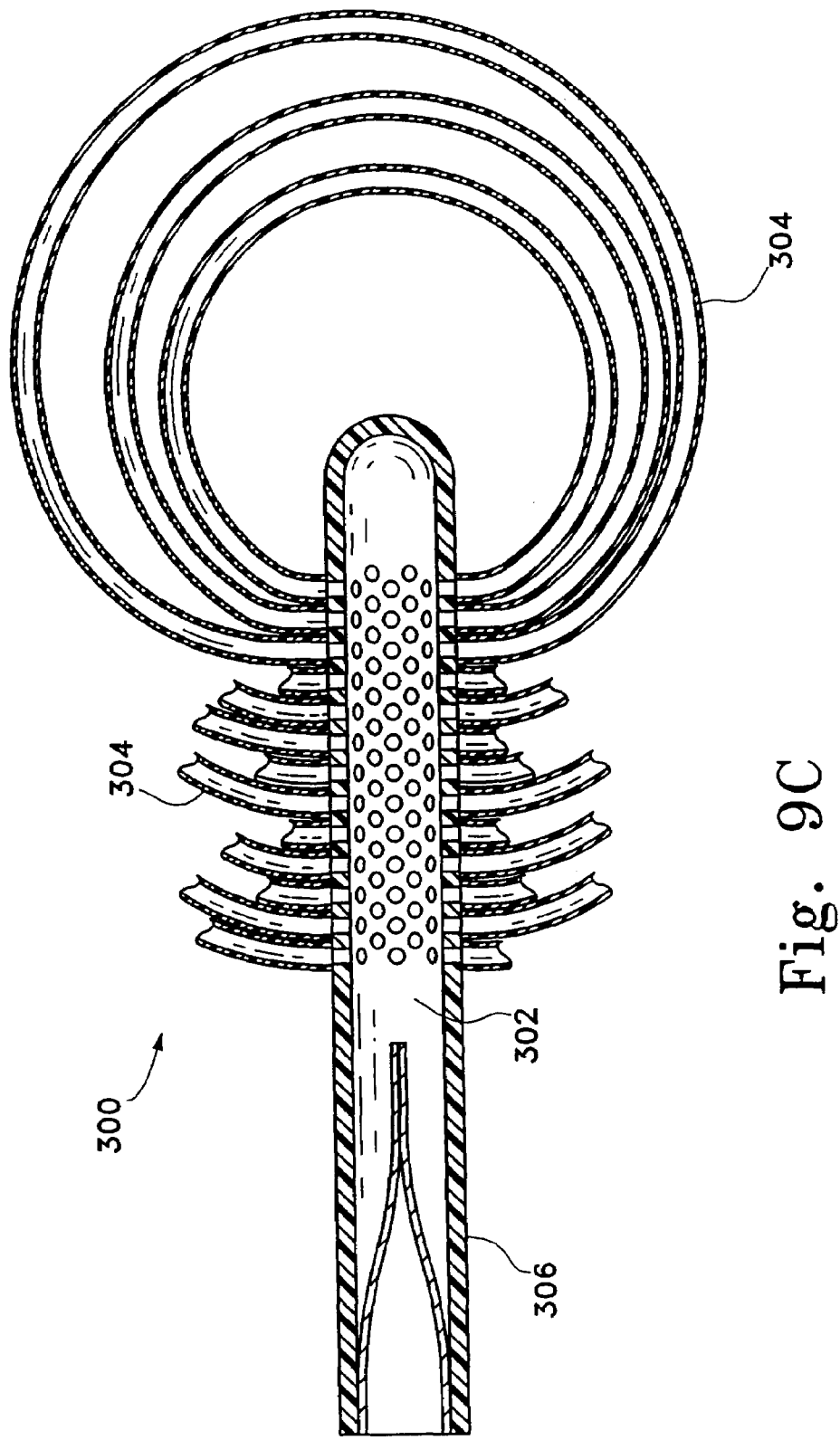
FIG. 9C is a partial cross-section of an implant having looped, fibrous portions in the implant.

A device such as that shown in FIGS. 7A, 7B, 7C and 7D may be perceived as having a potential problem with introducing filler into distant regions of the narrow bladder volume. Many highly desirable filler materials are viscous or have other nonlinear flow characteristics that make remote filling of the implant difficult. Consequently, a designer specifying the dimensions of the implant and the composition of the filler materials might choose any of a number of solutions to such a problem. For instance, such a designer might choose a less viscous filler material and utilize a catalyst or accelerator to gel the filler material once the filler material is introduced into the bladder volume. Indeed, such polymerization catalysts and accelerators may be applied interior to, perhaps, a portion of the bladder wall. Other mechanical flow-improving design procedures might include solutions such as are shown in FIGS. 9A, 9B, and 9C.

Figure 7E:
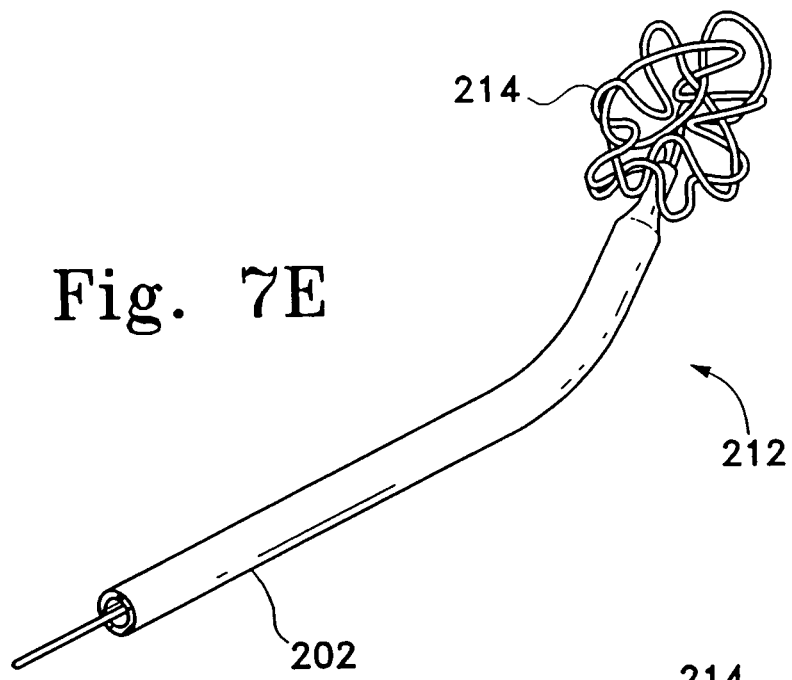
Figure 7F:
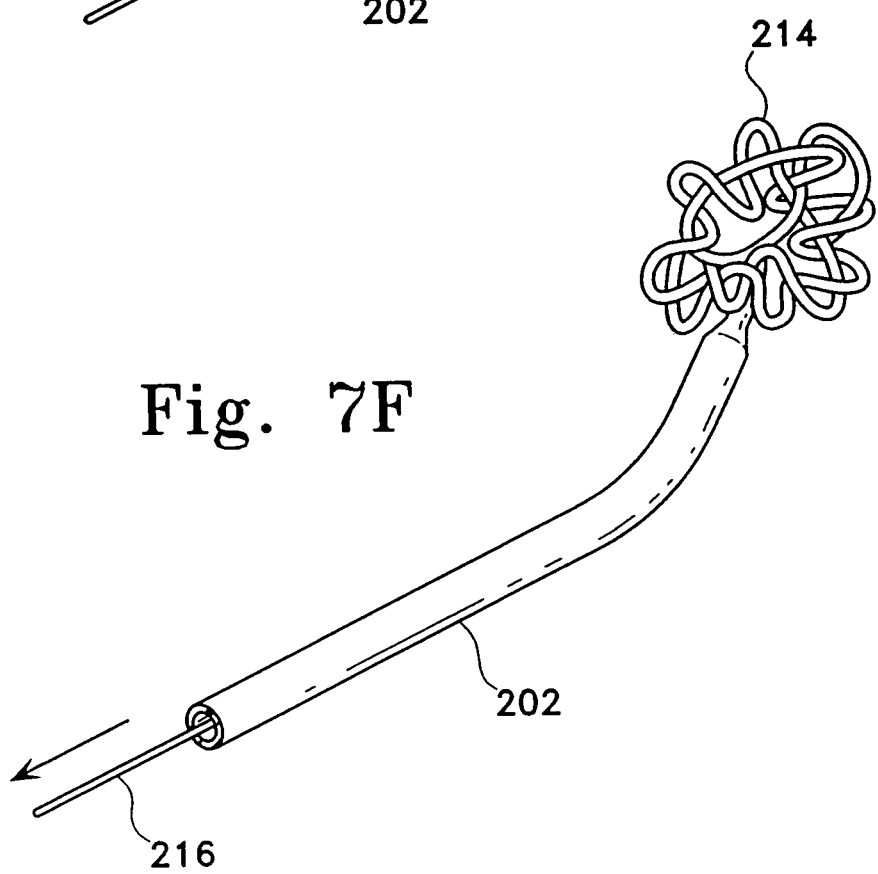

FIGS. 7E-7H show a variation of the implant system (212) in which the concept of a removable "batten" or "template" is shown. The deflated implant (214), seen in FIG. 7E for this example, may be the same as that seen in FIG. 7A except that the interior volume is adapted to allow the presence of a multiple armed batten (216) (as seen in FIG. 7H). The batten (216) allows the user to manipulate the deflated implant (214) into a shape or position prior to inflation or, perhaps after filling the implant with filling material. FIG. 7F shows the implant (214) after inflation with the filling material.

FIG. 7G shows the implant (214) after inflation with the filling material, withdrawal of the batten (216), and release from the filling catheter (202). Removable battens may be more complex or simpler in configuration than is shown as batten (216) depending upon the use. Such a batten may be used with any variation shown here. In addition, batten (216) need not be removed but optionally may be left behind in implant (214). Batten (216) may consequently take on a different configuration than that shown in FIGS. 7E-7H depending on whether it is intended to be removed as shown or left behind in implant (214).

FIG. 8 shows one suitable simple introduction region (210) for devices such as are shown in FIGS. 7A, 7B, 7C and 7D. Incidentally, the inflated size of such an implant varies as needed by a particular indication such as an aneurysm.

For instance, it is typical that an aneurysm in the brain is rarely much larger in diameter than one-half inch and normally not much over a quarter-inch in average diameter.

FIG. 9A shows in partial cross-section an implant (250) where the bladder wall (252), once inflated, resembles a burr or vintage shipping mine. This device includes a central chamber (254) with a number of openings (256) extending out into the hollow "spikes" (258) providing the significant surface area often desirable for forming thrombogenic surfaces. The opening (260) into the bladder volume including central volume (254), is shown in a somewhat schematic fashion. In this variation, the filler material flows into the central chamber (254) and then is faced with a number of flow paths into the tendrils extending from that central section of the device. This enhanced number of flow paths aids in permitting flow of these fluids into the spikes. It may be apparent to one of ordinary skill in this art that it would not be necessary that each of the "spikes" be hollow, but some may merely be solid appendages that, when the central chamber (254) is expanded will simply extend radially outward. As noted above, it is within the scope of this description that the interior of bladder wall (252), and particularly in the region of the central chamber (254), be provided with an accelerator for polymerization of multi-component precursor filler material.

Again, a device such as this is very simple to introduce into a saccular aneurysm in, e.g. the vasculature of the brain, since the implant need be placed only one time and filled.

FIG. 9B shows a conceptually similar solution to the problem of providing adequate flow paths for filler material where the implant is to have a large external surface area and a narrow bladder volume or narrow volume sections. In this example, the implant (270) includes multiple entries into the device bladder wall (272) and simply provides additional flow paths to a downstream chamber (274) that, in turn, fills hollow fibrils (276). The hollow fibrils (278) emanating from the primary bladder chamber (280) receive filler material only from feed device (282). The second chamber or portion of the bladder volume (274) receives filler material both from feed device (284) and from filler device (282). Various sections of this example of the implant are shown to be separated in a somewhat exaggerated fashion. For instance, the two filler supply devices (282) and (284) may be integrated into a single shaft cooperating in shape with a two-port, single opening in the bladder wall utilizing bypass pathway (286) to secondary chamber (274).

Another variation of this solution is to loop the hollow fibers of the extended bladder wall. The narrow openings in the fibers are then filled from two ends at the same time. FIG. 9C shows a device (300) having a complex interior volume made up of chamber (302) from which extend a number of hollow fibers (304). Those fibers that are hollow and each fiber lumen ends and begins at the bladder wall (306) surrounding volume (302).

As another non-limiting example of the versatility of the implant described here, FIGS. 10A, 10B, and 10C show a variation of the implant (400) that may be used to close the neck of a small-neck aneurysm (402). The shape of implant (400) and its placement in the neck of aneurysm (400) are shown in FIG. 10A. Such an implant form may be used by itself to close such aneurysms or used in conjunction with other occlusive devices placed previously in the aneurysm. FIG. 10B shows the implant (400) with its deflated shape, prior to introduction into the treatment site, and attached to a delivery catheter which, in this instance, serves as a filler material delivery device. In FIG. 10C, implant (400) has been expanded to show its shape prior to removal of the filler material delivery device (404).

Figure 10D:
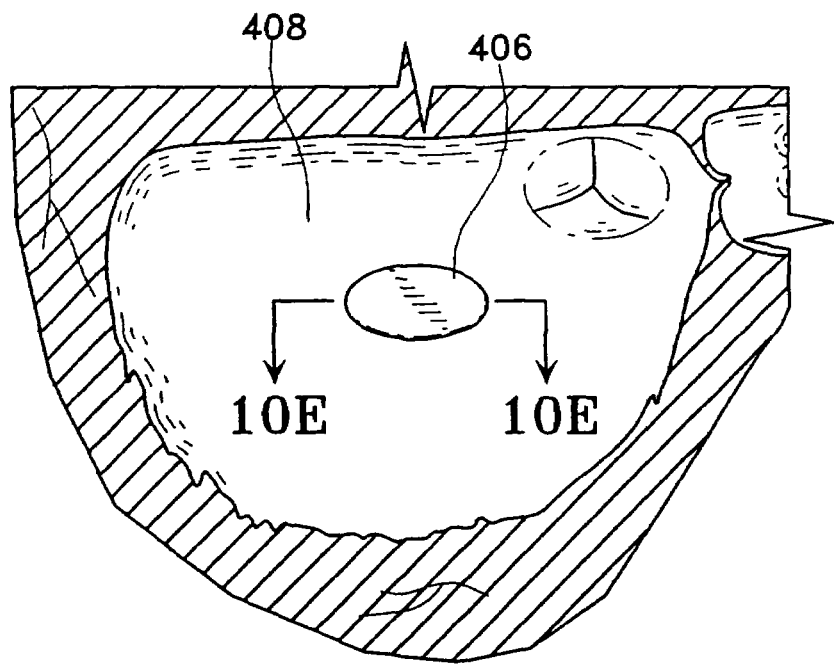
FIGS. 10D and 10E show, respectively, a perspective and a sectional, side view of a plug-like, occlusive implant in a septal defect.
Figure 10E:
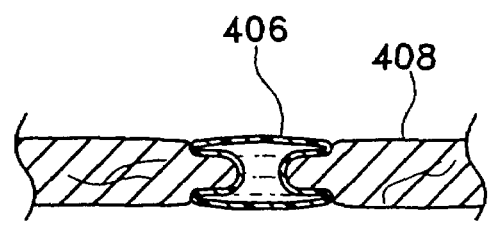

An implant having an appropriate shape such as found in FIGS. 10A-10C may similarly be used to repair interventricular septal defects. FIGS. 10D and 10E show placement of an implant (406) into an opening in the muscular interventricular wall (408). Delivery may be via catheterization procedures well known in interventional cardiology.

The set of implants exemplified above, demonstrate the facility and versatility with which this concept may be applied to a large number of body sites, particularly where an interior opening, be that opening a lumen, a sac, a duct, or an os, is to be filled, supported, or treated.

When our implants are used to occlude, they may be used in cooperation with ancillary components to assist in their function of occlusion. For instance, FIGS. 11A, 11B, and 11C show various ways of immobilizing or fixating the implant at a site to be occluded. Again, these are but examples of the generic concept of immobilizing or fixating the implant where an implant designer choosing or completing a specific design utilizes the teachings here to make a specific device for implementation.

FIG. 11A shows a partial sectional view of an implant (450) having a bladder wall (452) and a band of nubs (454) situated on the exterior. The nubs (454) are intended to engage the wall of a lumen or the like upon inflation of the implant in the body.

Similarly, FIG. 11B shows an implant (456) having a stent-like component (458) that includes a number of hooks (460) or barbs designed to engage a wall of lumen to which the device (456) was placed. The stent-like component (458) may also provide some additional structure support to the device (456) and may aid in filling the implant with filler material.

FIG. 11C shows another example of the device (456) having a stent-like structure (468) deployed on the exterior of a bladder wall (470). In this variation, as was the case with the variation shown in FIG. 12, the stent-like structure may be self-expanding upon deployment and be produced of a material such as a suitable stainless steel, a super elastic alloy such as nitinol, or any other material that is appropriate for this particular task. Similarly, the stent-like structures may be of a type that are expanded by the introduction of filler material into the bladder volume within the bladder wall (470) and may be simply malleable enough to maintain their shape at deployment. These structures may be used to provide stability to the desired shape of the implant after deployment.

Another desirable ancillary component is a radiopaque marker mounted on the bladder wall (482) of implant device (484). A marker such as radiopaque band (480) permits a medical professional accurately to place a device within the human body and, once so-placed, identify at a later time whether the device is still situated properly. Although the radiopaque band (480) depicted in FIG. 12 is shown to be circumferential and near an end of an implant, a designer may obviously place appropriate radiopaque markings at any suitable place on a device made according to these teachings. Such markings may aid or assist in proper placement, inflation, identification of the device, or whatever other function is then desired.

Other ways to provide or impart radiopacity to the implant include, for instance, placement (perhaps by ion-sputtering) of a radiopaque material such as gold onto the implant, including a powdered radiopaque solid such as barium sulfate in polymer of the bladder wall, or by introduction of a radiopaque dye into the bladder wall.

FIGS. 13A-13F show an implant (486) that is designed to be implanted in and to occlude a lumen such as a Fallopian tube or vas deferens, and then to be optionally removed. These drawings also show a delivery arrangement that may be used with many of the implant variations described here, in which a sheath is used over the implant during delivery and removed during deployment.

FIG. 13A shows an implant (486) having a support and retrieval wire or member (487) and a fill valve region (488). The implant (486) is covered by sheath (489) for delivery. A fill tube (490) is in the fill valve region (488) of the implant (486). Finally, a safety wire (492) having a pigtail end (494) located within the lumen of fill tube (490) is shown holding the implant (486) in place until deployment is desired.

FIG. 13B shows the pullback of the sheath (489), the movement of the filler material (493) through fill tube (490) and fill valve region (488) into the implant (486). The safety wire (492) has been rotated and has disengaged from support and retrieval wire (487). The support and retrieval wire (487) may be of a looping design that allows it to expand upon release of the sheath (489) and provide a measure of form to the implant (486) and of seal force against the vessel (494) wall. The support and retrieval wire (487) may have a section extending outside of the interior implant volume. FIG. 13C shows the inflating implant within the vessel (494) wall and the fill valve region (488) still open and accepting filler material.

FIGS. 13D and 13E show fill tube (490) having withdrawn from fill valve region (488) and support and retrieval wire (487) expanded to its full size within the implant (486) volume. FIG. 13E shows implant (486) fully expanded against the vessel (494) wall and closure of the fill valve region (488) over the support and retrieval wire (487). The implant is fully functional as an occluder in FIGS. 13D and 13E.

FIG. 13F shows removal or retrieval of implant (486). A retriever tube (495) having a retriever (496) has been introduced into the vessel (494) and the retriever (496) twisted to engage the support and retrieval wire (487). Proximal movement of the retriever (496) either moves the implant (486) or moves the support and retrieval wire (487) collapsing the loops of the support and retrieval wire (487) into the fill valve region (488) allowing the biocompatible filler to escape. All of this collapses and loosens the fit of the implant (486) within the lumen allowing it to follow the retriever tube (495) and the retriever (496) out of the vessel.

Figure 14A:
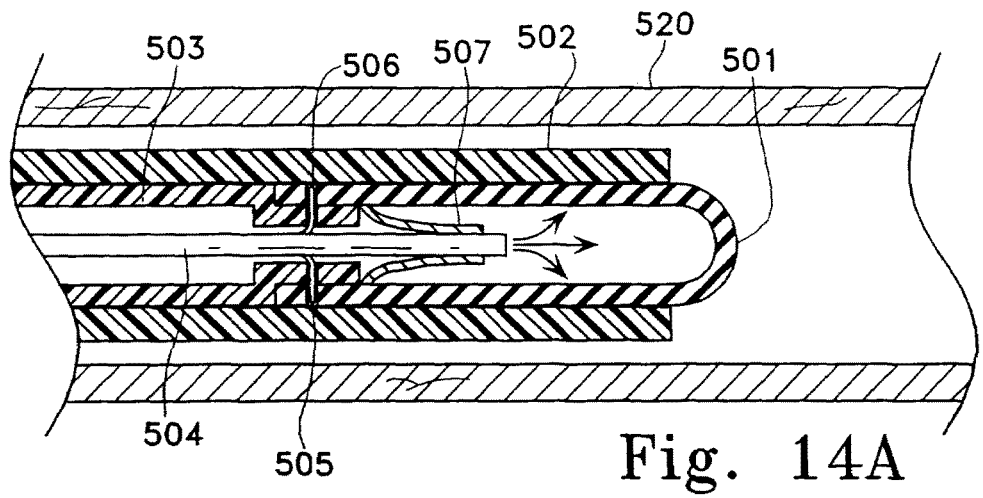
FIGS. 14A-14C show longitudinal, sectional views of an implant that may be retrieved after delivery and the sequence involved in placement and in retrieval. This example of our implant includes an integral site for retrieving the implant.
Figure 14B:
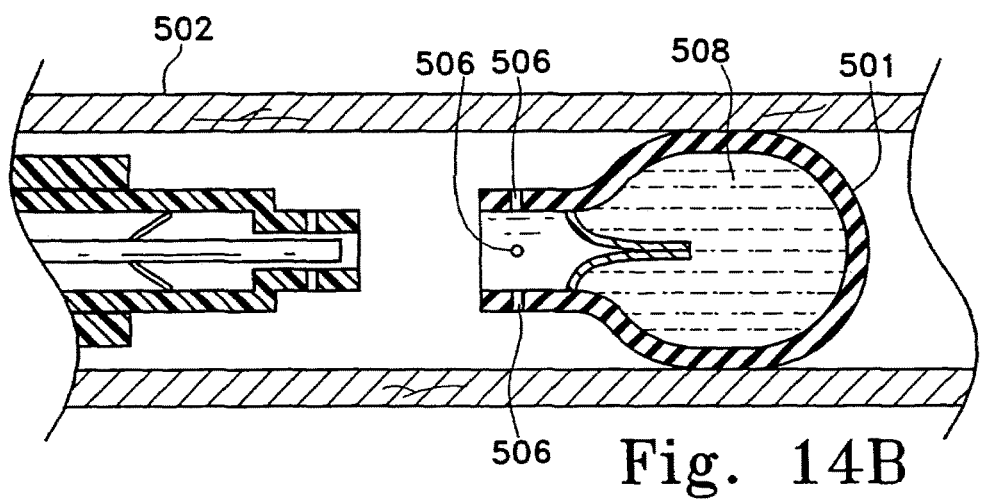
Figure 14C:
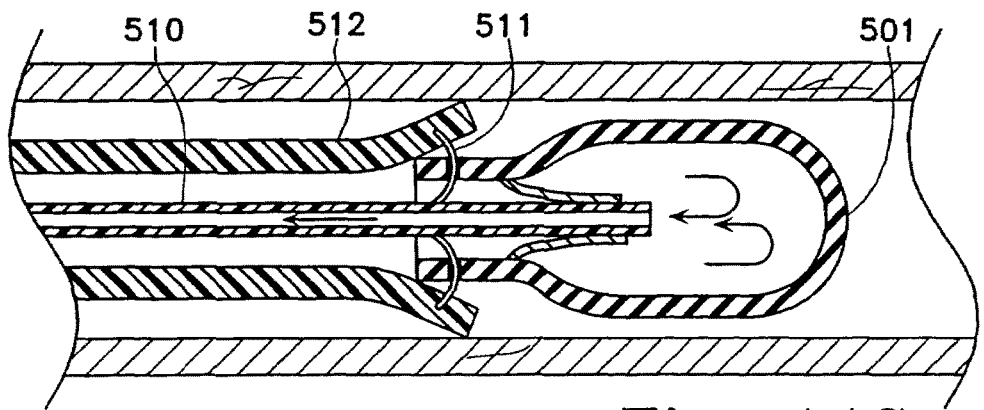

FIGS. 14A-14C show longitudinal, sectional views of an implant that may be retrieved after delivery, the use of integral retrieval sites in the implant, and the sequence involved in placement and in retrieval.

FIG. 14A shows an implant (501) that has been introduced into the lumen of a tubular member (520) of the body. An optional retractable sleeve (502) is situated outside of the implant (501). The implant (501) is mounted distally on a delivery member (503). A filler-retainer member (504) having extensions (505) that pass through openings (506) in the distal end of implant (501) is also shown. The distal-most end of filler-retainer member (504) also is shown passing through the illustrated fill valve and closure (507) situated in the implant (501). The filler-retainer member (504) in this example of the implant assembly has the functions of holding the implant (501) in place by interference of the extensions (505) in openings (506) during the step of placement at the treatment site, of holding the implant (501) in place at the end of the delivery member (503) during the filling step (after the optional outer sleeve (502) has been withdrawn), and of acting as a passageway for the filling materials (508) during expansion of the implant (501) bladder.

FIG. 14B shows the implant (501) in place acting as an occluding member in the vessel (520) with the filler material (508) within the volume inside. The various openings (506) acting as integral retrieval sites are shown. Previously, the optional retractable sleeve (502) has been retracted, the filler-retainer member (504) has been withdrawn allowing extensions (505) to pull from openings (506), and the delivery member (503) has also been retracted. Each of optional retractable sleeve (502), the filler-retainer member (504), and delivery member (503) extend to the users' end and typically would be independently manipulable.

FIG. 14C shows a typical way of removing implant (501) using a retriever (510) that cooperates with the openings (506) to grasp or otherwise secure the implant (501) to the retriever member (510) via engagement of the extensions (511) into the openings (506). In this example of the implant assembly, the retriever (510) also acts to bleed the filler material from the implant (501) interior volume. An exterior sleeve (512) may also be used to center the end of implant (501), if so desired.

As we have mentioned elsewhere, these implants may be used to perform the function of occluding openings in the body when they are placed within the opening. Additionally, our implant may be used to control or to close tubular passageways or ducts by squeezing those openings from the exterior of those tubular passageways. For instance, in addition to the fallopian tube closure shown just above, a sterilization procedure may be performed by placement of an implant on the exterior of the tube in such a way as to close the tube. The versatility of our implant is such that (depending upon the use and design) it may be used as a permanent closure device for such body structures, as a temporary (but later removable) closure, or as a component of devices that control passage through a body passageway under the control of the patient or their physician.

Figure 15:
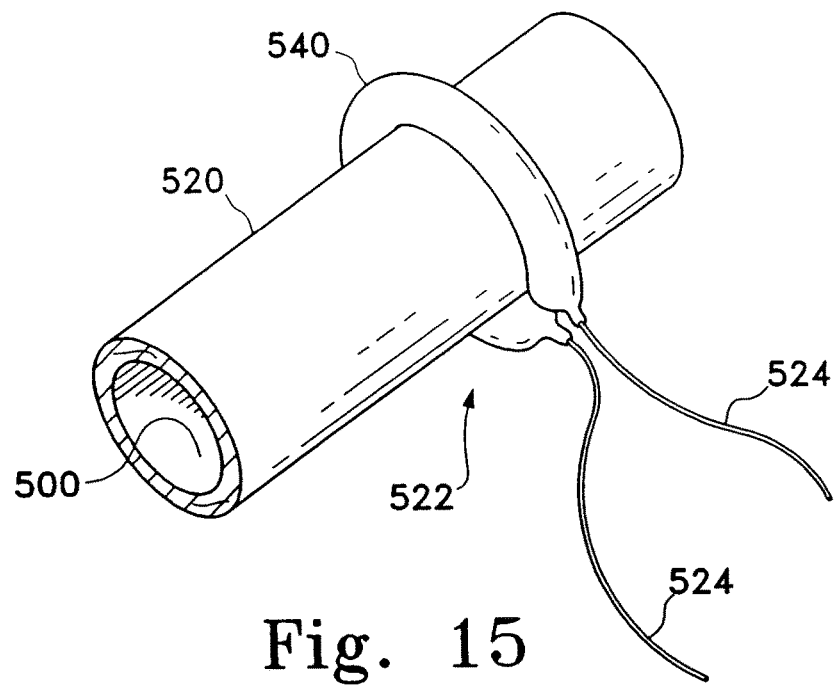
FIG. 15 shows a perspective view of a U-shaped implant that may be placed about a human body's tubular lumen.

FIG. 15 shows one method of occluding, or narrowing or controlling the size of a lumen in a tubular body member (520) using, in this instance, a loop-shaped bladder (540), that when inflated, will close the lumen (500) or narrow it depending upon the physical size of the implant (522) and the extent to which it is inflated. Shown attached to this example of the implant are tie lines (524) that may be used to secure the implant (522) to a nearby anatomic structures, perhaps when the implant (522) is used as a sling in assisting urethral control. Similarly, the tie-lines (524) may be used to secure the implant (522) onto the body tubular member (520).

Figure 16:
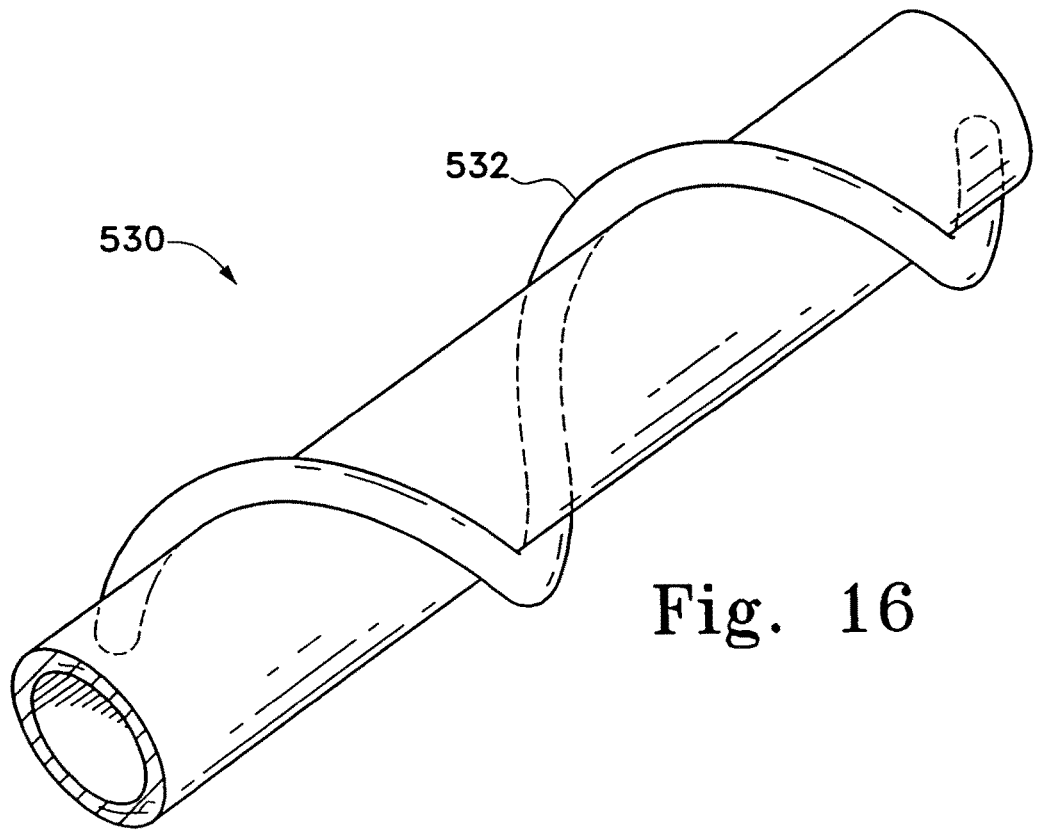
FIG. 16 shows in perspective, a generally helical implant forming a support for a body tubular member or organ.

FIG. 16 shows another variation of the implant (530) having a simple helical shape. Since the implant (530) may be filled with filler material that is in situ polymerizable into a gel or even into a solid, the implant (530) may be filled, the filler material cured or hardened while being held in place, and the resulting structure used as an exterior supporting structure for the lumen or as a stabilizer structure for the tubular body member, perhaps in conjunction with an aneurysm. Bladder wall (532) is also shown in the FIG. 16.

Figure 17A:
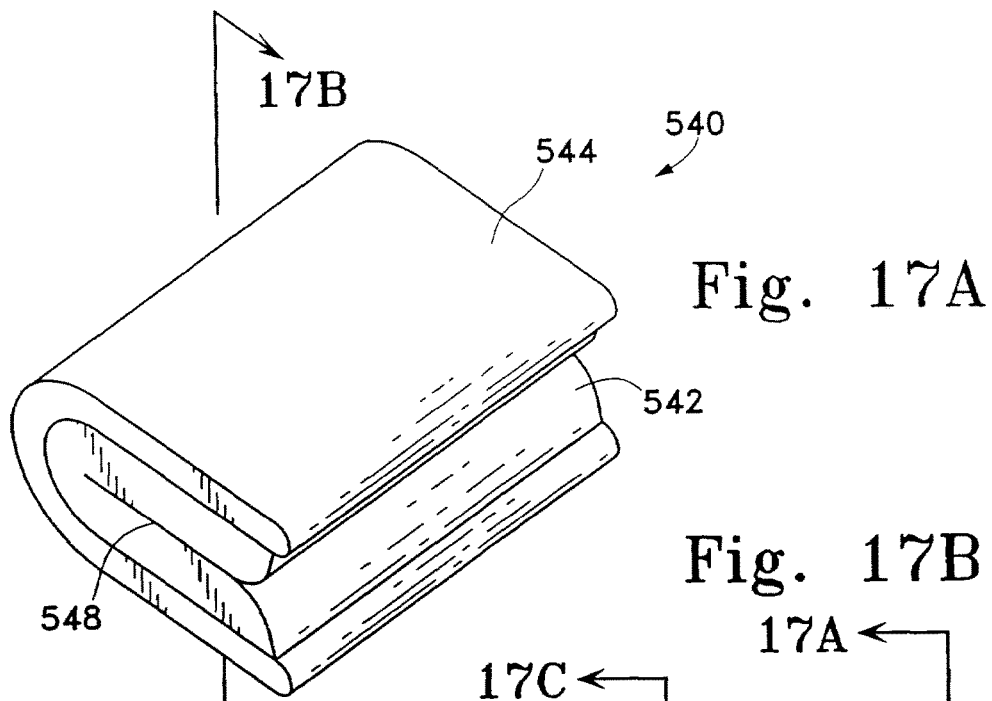
FIGS. 17A to 17C respectively show side view, end view and cross-sectional view of a multi-chambered implant.
Figure 17B:
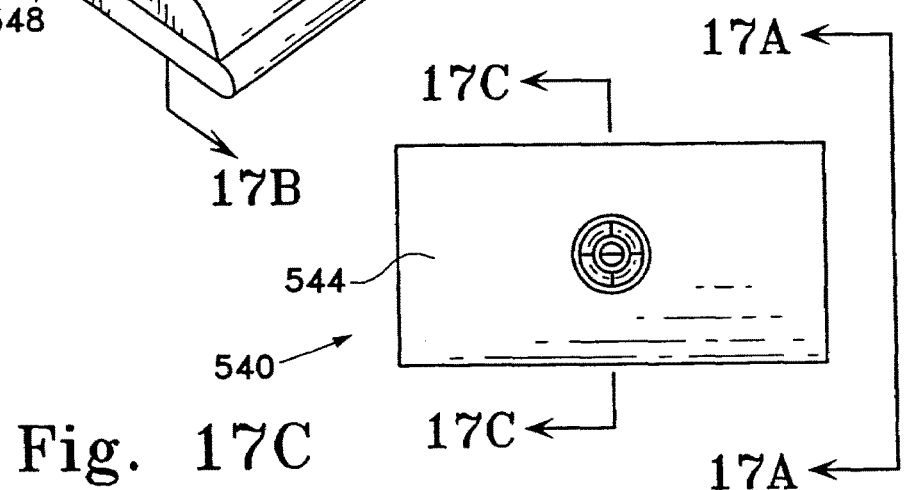

FIGS. 17A and 17B depict side and end views of an implant (540) having multiple independent bladder or bladder volumes. The shape depicted in FIGS. 17A and 17B may be used in those situations where an additional measure of turgor or support is needed, for instance, at a sphincter muscle controlling a bodily fluid flow or direction. This implant may be used (with proper sizing and adjustment of the respective bladder compositions, etc.) in treating such maladies as gastroesophageal reflux disease (GERD) and severe female urinary incontinence (FUI). FIG. 17A shows an inner bladder (542) and an outer bladder (544). In this variation of the multiple bladder implant, the bladders share a wall, the outer bladder (544) is intended to enclose a settable or curable filler material, the inner bladder (542) is intended to enclose a filler material that remains fluid or gel-like after introduction. This variation also exemplifies, for the scope of described implants found here, the generic application of elastic bladder walls, comprising elastomeric materials or other similarly expandable materials, in conjunction with bladder walls that are not elastic—at least as the concept of inelasticity is used in the medical device area. For instance, angioplasty balloons are often made of materials such as Nylon. When expanded, those balloons expand to a specific diameter, but not more. Nylon is considered to be inelastic in a practical sense for those purposes.

In any case and for the purposes of this example, the implant (540) may be constructed with an outer bladder (544) of an inelastic material and an inner bladder (542) comprising an elastic material. Often, treatment of severe instances of diseases such as GERD entail the surgical addition of a muscle structure to the offending sphincter muscle structure. From an engineering viewpoint, the added muscle does not provide significant added strength. The multi chambered "clip" shaped implant (540) shown in FIGS. 17A, 17B, and 17C can be constructed to provide a firm assist to the sphincter muscle structures without major surgical intervention. The outer bladder (544) provides flexing strength by compression of the region between the two opposing sections or arms of the bladder. The inner bladder (542) may be provided with a compliant inner surface (548) by use of both of (or, either of) an elastic material and a non-setting filler, e.g., a gel or liquid. The inward pressure onto the surface (548) may therefore be adjusted in many complementary ways.

Figure 17C:
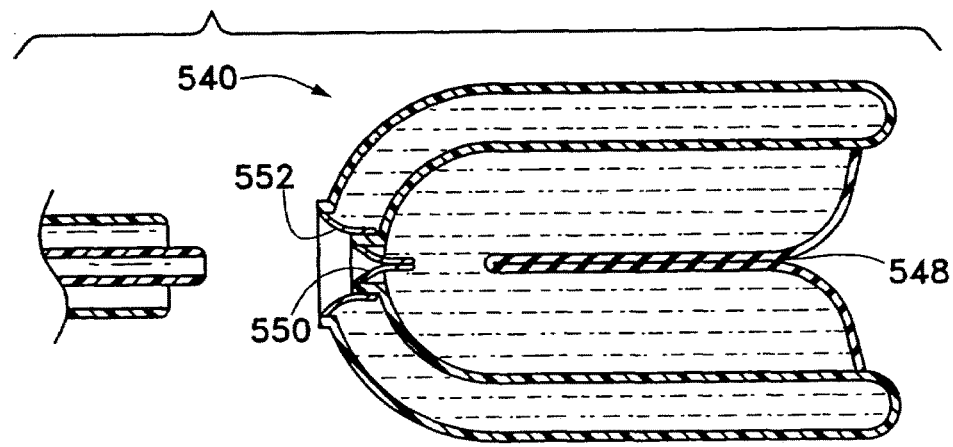

FIG. 17C shows a cross-section of the implant (540) with the outer bladder (544), the inner bladder (542), and the fill valves (inner 550, outer 552). A filler member (554) is also depicted that may be used to independently fill the two bladders.

Figure 18:
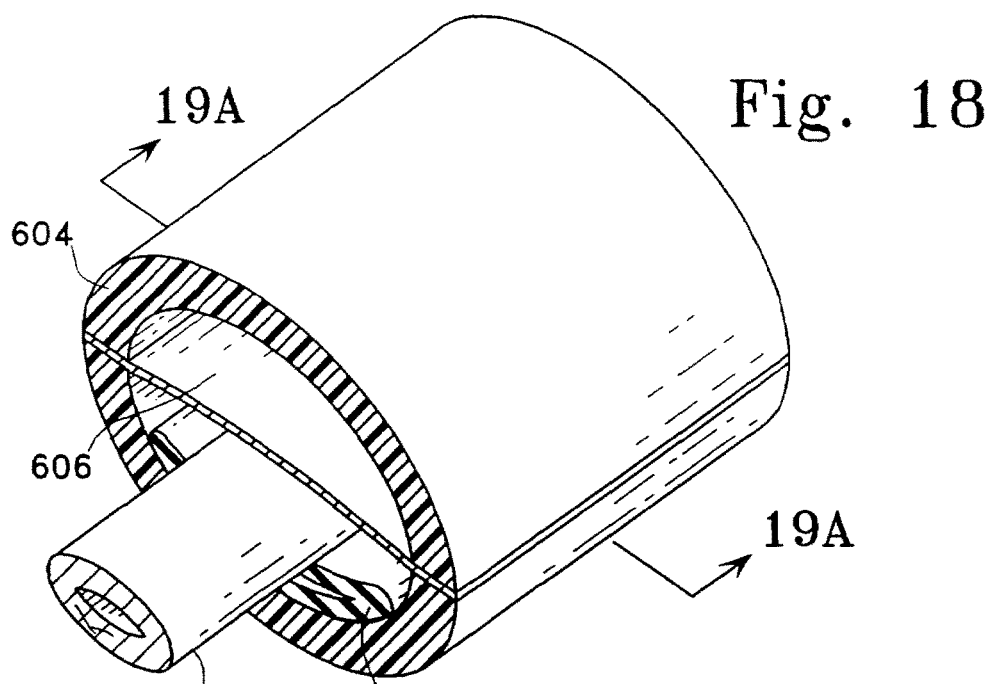
FIG. 18 shows a valving assembly that may be used to close a human body duct or other bodily tubular member. This example of our implant is used in coordination with a spring to hold the body lumen closed.
Figure 19A:
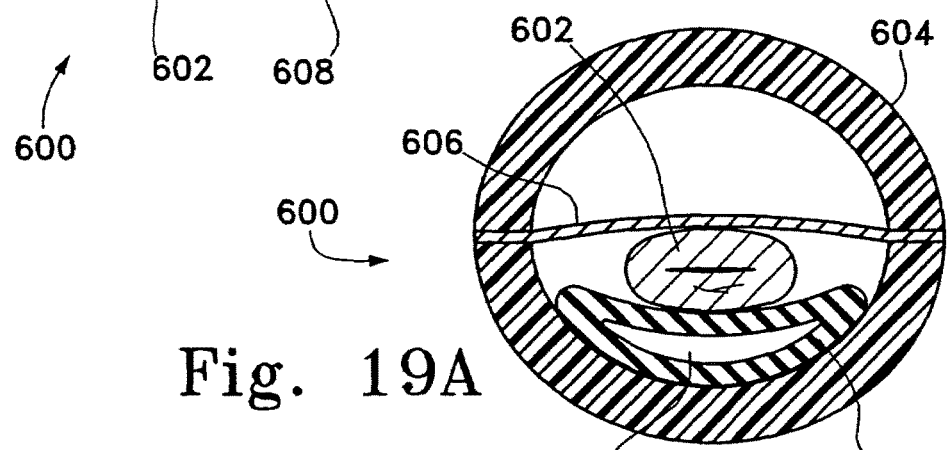
FIG. 19A shows a cross-section of the device found in FIG. 18 during the "relaxed' position.
Figure 19B:
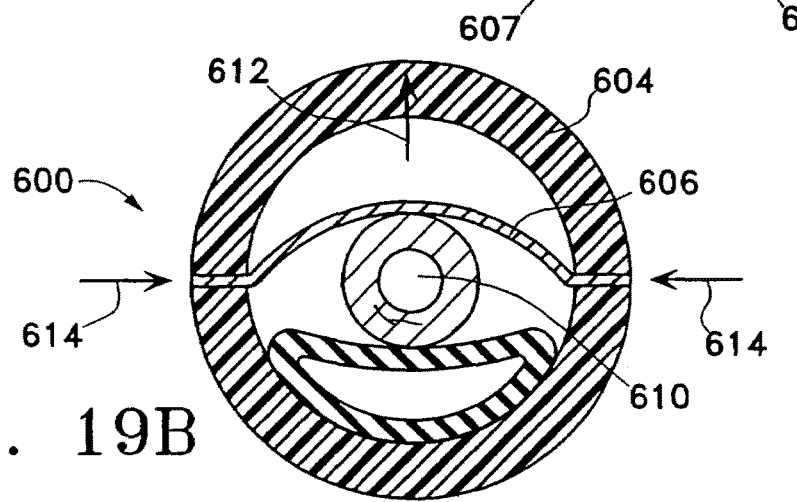
FIG. 19B shows the body lumen open for movement of the bodily fluid through it.

FIGS. 18, 19A, and 19B show the use of the implant as a source of motion or pressure for controlling a valve assembly that may be placed in the human body, for instance, in treating GERD or FUI using active manipulation. The operating concept of the depicted valving device (600) is that the tubular member (602) is typically closed due to the forces exerted upon it by the flexible, perhaps springy, housing (604) and by the spring member (606) bias. In this instance the inventive implant (608) is used to "tune" the residual pressure placed against the tubular body member having the lumen. In one example of this valving assembly (600), the overall pressure of the depicted spring (through the tubular body member) against the implant is selected so that the person into whom this device is implanted is able to urge or push fluids through the tubing using their own muscles. For instance, in assisting with control of urinary voiding, the stiffness of the housing (604), the spring member (606) and the amount of filler material introduced into implant (608) are chosen, after testing of the patient, so that he or she can push urine past this valving assembly using typical abdominal muscles. FIG. 19A shows a cross section of the valving assembly (600) shown in FIG. 18 during the time the tubular body member (602) is closed by a valving assembly (600). It may be noted that the upper and lower portions of housing assembly (604) are shown to be separable. Although this is not a necessity, it is convenient for installation and later removal if muscle vigor of the patient declines with time. Other convenient spring and housing arrangements would be apparent upon this description. Similarly other sources of spring bias or springiness, e.g., balloons or other internal organs, may also be used in this device. Bladder volume (606) and bladder wall (608) are shown as cooperating with the spring member and body (604) to close the lumen shown there.

FIG. 19B shows the opening of lumen (610) by, e.g., the implantee's movement of fluid via increased pressure through that lumen (610). When the patient so voids, the spring member (606) flexes in the direction (612) and the flexible housing flexes inward in the directions noted by arrows (614) and (616). When the pressure in lumen (610) ceases, the valving mechanism (600) returns to the state found in FIG. 19A.

FIGS. 20A, 20B, and 20C show another variation of a valving assembly using our implant. In this example, the implant includes both inelastic and elastic components in communication with the filler material. FIG. 20A shows a body tubular member (632) surrounded by a ring or housing member (634) having an open center, which ring member (634) may be elastic or more likely, inelastic. Situated within the ring is an inelastic portion (636) of the implant (630). The implant (630) is filled with a filler material that is sufficiently mobile, perhaps fluid, so that a slight pressure is placed by the bladder wall (636) against the body tubular member (632) to maintain closure of the body lumen. However, as was the case with the implant shown in FIGS. 18, 19A, and 19B, the patient may urge his bodily fluids through the body tubular member (632). When this happens, the portion of the implant (630) beneath the ring is compressed and filler material flows into the elastic sections (638) of the device (630). The movement of the exterior wall of the implant (630) is shown to be moved at arrows (640); such a movement allows the patient's body tubular member to open and fluids to flow. When the pressure interior to that lumen within the body tubular member (632) is relaxed, filler material within the elastic sections (638) will return to the region beneath ring (634) and the wall contacting the tubular member (632) will press against that body member in the directions shown by arrows (642) and close the interior body lumen.

Figure 21A:
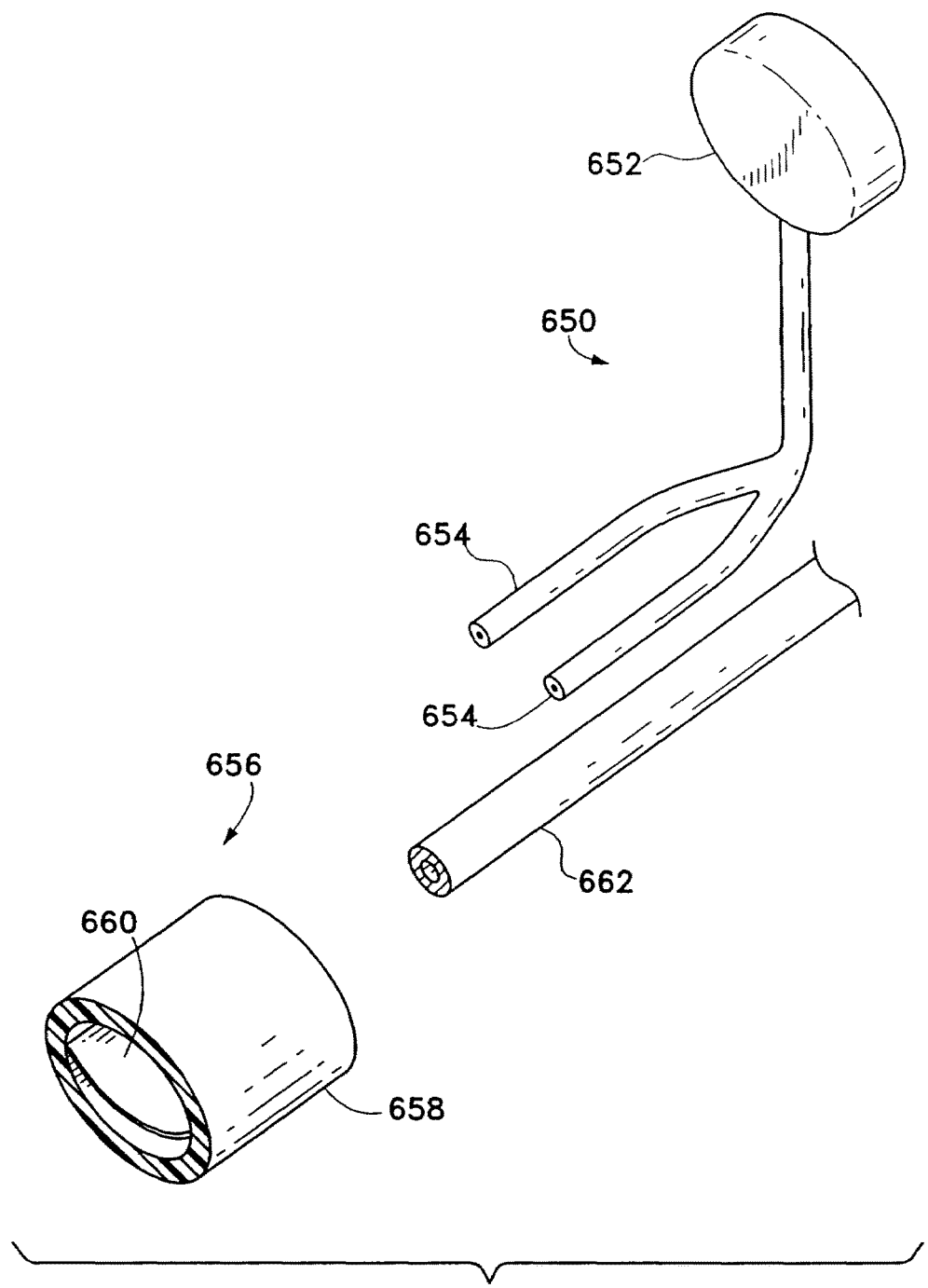
FIGS. 21A, 21B, and 21C show a valving assembly utilizing an implant that may be used in controlling or stopping flow through a human body lumen. The implant is used to open the included valve and the lumen. The device may be configured to be manually controlled by the user.
Figure 21B:
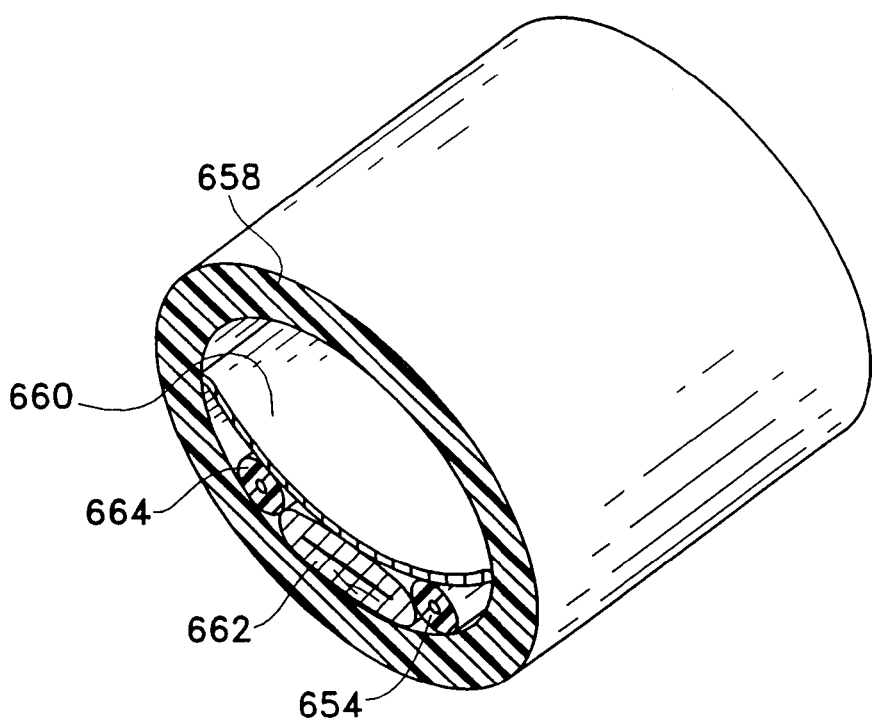
Figure 21C:
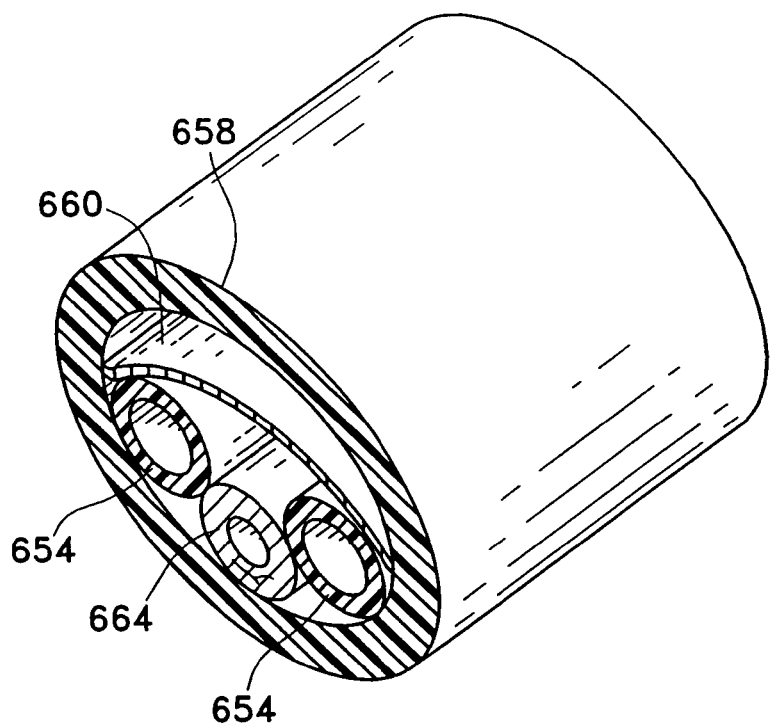

Another use of our implant is shown in the valving assembly shown in FIGS. 21A, 21B, and 21C. In this example, the implant (650) is used to move a spring member biased to close a body lumen to a position where the body lumen is open by manipulation of, or palpation of a portion of the implant.

FIG. 21A shows the major components of the valving assembly. The implant (650) is shown in FIG. 21A with a palpation reservoir or bulb (652) at one end of the device and with a pair of expandable fingers (654) (or, generically, "motive sections") at the other extremity of the implant. This example is shown with two fingers (654) and, as will be explained below, during placement and use of the device it is necessary in this variation that the fingers be held in such a way to be spaced apart from each other. Otherwise, during a filling operation, the fingers will move together and squeeze the involved body duct. Other suitable arrangements using a single finger or more than two fingers would be apparent upon simple reflection. FIG. 21A also shows the housing spring subassembly (656). This is made up of a housing member (658) and a biased spring (660). The body tubular member (662) that is to be under control by this device is also shown.

The implant (650) in this variation is not to be filled to its maximum possible volume if inelastic bladder wall materials are to be used. The sizes, volumes, filler material/fluids, should be selected in such a way that when the palpation bulb (652) is squeezed, the fingers (652) are able to expand and move the spring away from the body tubular member.

FIG. 21B shows a partial perspective cutaway of the "normal" or non-actuated or resting state of the device after implantation. It should be noted that although we have chosen not to show the housing member (658) with a seam or other way to place the body (658) about the body tubular member (662) some manner of placing the housing about the body tubular member (662) is necessary. Other designs, perhaps using a "U" shaped housing would not be so constrained.

FIG. 21B shows the housing member (658) and the spring member (660) biased downward to squeeze the body tubular member (662) to close its lumen (664). Also shown are the two fingers (654) of the implant (650). As was the case in discussing the device found in FIGS. 18, 19A, and 19B, housing member (658) may be stiff or, more likely may be somewhat springy. A biocompatible, elastomeric material would be appropriate for this part. Interior to housing member (658) may be seen spring member (660). Spring member (660) is a biased downward and made of material that may be moved by inflation of fingers (654).

FIG. 21C shows the desired action of the inflation of fingers (654) to move spring member (660) upward and allow the opening of body lumen (664). Upon release of the pressure on the palpation bulb (652), the spring (660) should relax into the position found in FIG. 21B and close lumen (664).

The assembly shown in FIGS. 21A, 21B, and 21C is to be placed within the body using a surgical procedure. The bulb (652) may be placed in such a position that it can be manipulated by the person into whom the implant has been placed using, for instance, the strength in a hand to open the valve assembly. For instance, where the implant shown in FIGS. 21A, 21B, and 21C is to be used for bladder control, the palpation bulb would be desirably placed beneath the skin of the lower abdomen at a site where the bulb (652) would not be easily bumped nor would it be squeezed upon normal clothing binds or the like. The size of the bulb (652) in such a situation need not be very large in that little fluid would need to be moved, in turn, to move the spring releasing the urethra.

Bladder Wall Materials

To allow selection of a desired controllable size for the implant where the size need not be adjusted after introduction into the body, the bladder wall material may be non-elastic and of a biocompatible fabric. In many instances, the implant designer using the teachings found here will choose to form the implant from a single material. Suitable polymers that are formable into continuous structures or forms (e.g., sheets, tubes, etc.), fabrics (woven and non-woven), and ancillary components, e.g., portions of the valving, and that are biocompatibly suitable as long term implants, are currently but a few: polyethyleneterephthalate (PET or "Dacron"), polyvinylchloride (PVC), various polyurethanes, polyolefins (various polyethylenes, polypropylenes, polybutylenes, and random and block copolymers), various polyamides (in particular, the Nylons), and fluoropolymers (such as polytetrafluoroethylene (PTFE or TFE), poly (ethylene-chlorofluoroethylene) (ECTFE), poly(fluorinated ethylene propylene) (FEP), polychlorotrifluoroethylene (PCTFE), polyperfluoroalkoxy (PFA), polyvinylfluoride (PVF) or polyvinylidenefluoride (PVDF)), and porous and expanded polytetrafluoroethylene (ePTFE).

The materials most widely currently used for implants, such as synthetic vascular grafts, are likely PET in the form of Dacron® and ePTFE in the form of ImpraGraft® and Goretex®. Those materials similarly suitable for many of the uses contemplated here. The current medical experience with these materials allows the designer to make an appropriate materials selection for an intended use. For instance, in the implants specifically designed for later removal or designed for potential later removal, such as those used in semi-permanent birth control, for instance, as an occlusive sterilizing plug to be situated in the Fallopian tube or vas deferens, a material having a physical structure, e.g., microstructure, with very low permeability to the ingrowth of the neighboring tissue would be a good selection. Similarly, implants used for filling vascular aneurysms desirably are constructed of materials having a significant potential for tissue ingrowth.

In those variations of the described implant where the filler material acts as a "sink" or reservoir of a treatment material of some kind, e.g., medication, anesthetic, analgesic, antibiotic, biologic, etc., a bladder wall material should be chosen having an appropriate permeability and thickness allowing release of that treatment material at the chosen site. The variations in which the implant is used for retention of ill-actors, such as trace metals, criteria for selecting the bladder wall material should include at least its ability to allow passage of the bad actor to the filler material.

When the bladder is used as a radio frequency energy sink (as discussed below), some amount of carbon fiber, e.g., pyrolyzed polyacrylonitrile or the like, or other radio-frequency absorbing materials such as metal or alloy fibers, may comprise the bladder wall, or be added to the mix of materials making up the bladder wall or be made adherent to the bladder wall in the region where desired.

The use of combination or laminated bladder wall materials is also contemplated. For instance, use of an elastomeric or rubbery material (sheets, non-continuous regions, etc.) exterior to the substantially non-elastic bladder wall material as a method of anchoring or otherwise maintaining the implant in position is suitable. Addition of a porous or fibrous material, e.g., PET and mixtures of other fibers, on the exterior of a bladder wall selected for use in a vascular environment, for the specific purpose of promoting angio-genesis or thrombogenesis, is also within the scope of the technology disclosed here.

Finally, it is with in the scope of this invention that the bladder wall include independent regions of elastic materials, e.g., polyurethanes, polycarbonate urethanes, an elastomeric silicone materials in addition to the wall components of inelastic material.

Inflation Components

Introduction of a filler material into the bladder volume may be accomplished in a wide variety of ways and using any number of different components to pass the filler materials, e.g., fluid (or fluids), through the bladder wall and into the bladder volume. For instance, when precursor materials that are reactive in situ to set, or to form a gel or solid in the bladder volume over time are introduced into that volume, the chosen introducer device may simply be held in place to form a plug until the reaction is sufficiently complete and the gel or solid is extant. A simple opening in the bladder wall serves, in cooperation with the introducer, to maintain the filler in the bladder volume.

Figure 22A:
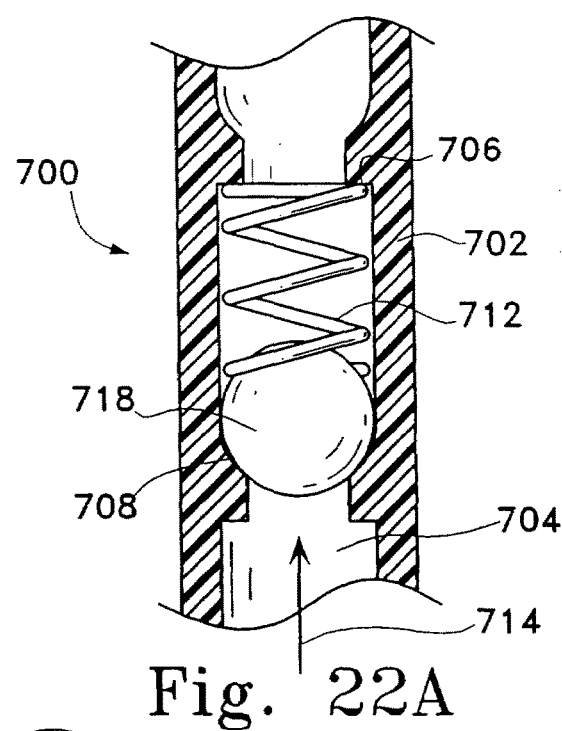
FIGS. 22A, 22B, and 22C show partial cutaway views of valves suitable for use in allowing filler materials into the bladder volume.
Figure 22B:
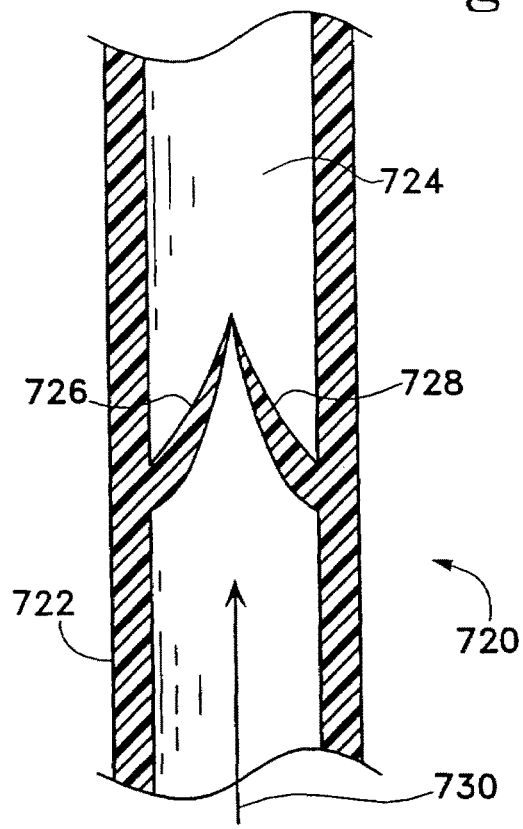
Figure 22C:
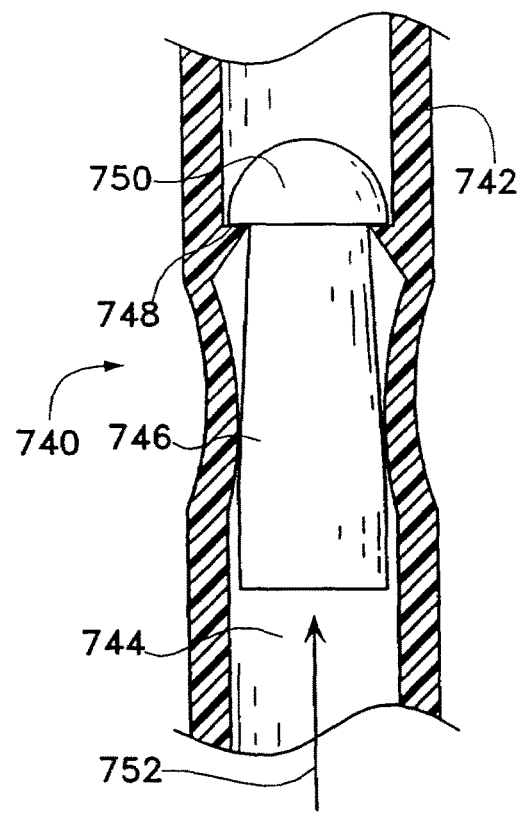

Normally, though, one or more optional one-way valves form the passageway through the bladder wall permitting flow into the interior bladder volume and preventing filler material flow out of the volume once either the bladder volume is filled or the introducer device is removed from the one way valves. FIGS. 22A, 22B, and 22C provide examples of such optional valves.

FIG. 22A is a longitudinal cross-sectional view of a spring-loaded inflation valve. The one-way inflation valve (700) has an outer wall (702), an inner lumen (704), an annular spring stop (706), an annular ball seal (708), a sealing body (710), and a sealing spring (712). The configuration depicted in FIG. 22A allows for introduction of a filler material in the direction of the arrow (714) while preventing its exit once pressure is removed.

FIG. 22B illustrates a duckbill-type one way valve. This exemplified one-way inflation valve (720) has an outer wall (722), an inner lumen (724), a first duckbill valve surface (726), and a second duckbill valve surface (728). The two bill surfaces are biased towards and seal against each other when the introduction device is removed and the valve assembly is relaxed. The valve depicted in FIG. 22B allows for movement of the filler material in the direction of the arrow (730) while preventing its exit once pressure is removed.

FIG. 22C illustrates an example of an insertable seal (740), operating much in the same way as does a wine cork, but one that cannot later be removed by normal means. The seal has an outer wall (742), an inner lumen (744), a plug (746), and a sealing surface (748). The plug (746) has a sealing head (750) which sealingly engages the sealing surface (748) by irreversible deployment during application of force to the plug (746) in the direction of the arrow (752).

Filler Materials

The bladder may be filled with a filler material, a convenient biocompatible material, that may be wide-ranging in nature. It may be a gas, if so desired, although in most circumstances, the filler may be a liquid, gel, or slurry. Convenient filler fluids include water, saline, and other fluids or gels such as those commonly employed in implants. Such biocompatible materials include triglycerides, (e.g., peanut oils), salts of chondroitin sulfate, salts of hyaluronic acid, various polyacrylamide compositions, various polysaccharides, hydroxypropylmethylcellulose polymers, and mixtures. Patient body fluids, e.g., blood, may be useful as filler materials in some circumstances.

As to other forms of the filler material: we have also had excellent experience with polymeric biomaterials, specifically polymeric hydrogels, that were specifically developed for medical treatments. They are of the type shown in WO 00/44808, to Hubbell et al, published Aug. 8, 2000, the entirety of which is incorporated by notice. These materials are made via addition reactions between a strong nucleophile and a conjugated unsaturation, for polymerizing or cross-linking two or more components in a manner that can be accomplished even in the presence of sensitive biological materials. Such reactions include the formation of biomaterials in the presence of drugs, including proteins and DNA, formation of biomaterials in the presence of cells and cell aggregates, and also formation of biomaterials in vivo variously, within the body, upon the surface of the body, or in a bladder as described above. It is possible to form these biomaterials in the presence of sensitive biological materials because of the high self-selectivity of the addition reactions between strong nucleophiles and conjugated unsaturations, that are employed. A strong nucleophile of particular interest in the method described herein is the thiol.

The formation of the noted biomaterial in the presence of the sensitive biological materials involves mixing two or more liquid components and reacting them to form an elastic solid, an inelastic solid, a viscoelastic solid (similar in consistency to a gel such as gelatin), a viscoelastic liquid (similar to a gel that can be induced to flow, for example, a petroleum jelly), a viscoelastic liquid that is formed of gel microparticles (such as a "Carbopol" gel), or even a viscous liquid of a considerably higher viscosity than either of the two precursor components. The chemical conversion from the precursors to the final material is sufficiently selective that it can be carried out in the presence of sensitive biological material without substantial side reactions, including the instance where the biological material is the body itself.

One family of such synthetic polymers may: (i.) be converted from liquid precursors to polymeric linear or cross-linked biomaterials prior to implantation or in situ at a site of implantation; (ii) be hydrogels or more substantially non-swelling materials; (iii) present bioactive molecules that serve as adhesion sites, to provide traction for cell invasion; (iv) present bioactive molecules that serve as protease substrate sites, to make the material degrade in response to enzymes (e.g., to collagenase or plasmin, that are produced by cells during cell migration); (v) present growth factor binding sites, and (vi) provide for the delivery of protein drugs by hydrolysis or enzymatic degradation of groups contained within the polymers forming the gel.

One variation of a method for forming a biomaterial, perhaps degradable, involves combining two or more precursor components of the biomaterial under conditions that allow polymerization of the two components, where polymerization occurs through self selective reaction between a strong nucleophile and a conjugated unsaturated bond or a conjugated unsaturated group, by nucleophilic addition. The functionality of each component is at least two, and the biomaterial does not comprise unprocessed albumin. In addition, the conjugated unsaturated bond or group is not a maleimide or a vinyl sulfone.

For instance, the components may be selected from the group consisting of oligomers, polymers, biosynthetic proteins or peptides, naturally-occurring peptides or proteins, processed naturally-occurring peptides or proteins, and polysaccharides. Of these, the polymer may be poly(ethylene glycol), poly(ethylene oxide), poly(vinyl alcohol), poly (ethylene-co-vinyl alcohol), poly(acrylic acid), poly(ethylene-co-acrylic acid), poly(ethyloxazoline), poly(vinyl pyrrolidone), poly(ethylene-co-vinyl pyrrolidone), poly(maleic acid), poly(ethylene-co-maleic acid), poly(acrylamide), or poly(ethylene oxide)-co-poly(propylene oxide) block copolymers.

The peptides may, for instance, comprise an adhesion site, growth factor binding site, or protease binding site.

In another variation, the components may be functionalized to comprise a strong nucleophile or a conjugated unsaturated group or a conjugated unsaturated bond. In this variation, the strong nucleophile may be a group such as a thiol or a group containing a thiol and the conjugated unsaturated group may be an acrylate, an acrylamide, a quinone, or a vinylpyridinium, for example, 2- or 4-vinylpyridinium. Either of the components may have a functionality of two, three, or more.

In some variations where acceleration of the reaction to form a gel is desirable, an accelerator may be added prior to polymerization. For instance, mixing of the precursor components with a component having at least one conjugated unsaturated bond or conjugated unsaturated group and at least one amine reactive group will accelerate the polymerization. Where cells are to be added to the resultant mixture, that accelerator may also be applied to the cell surface site of polymerization.

Where the biomaterial is used to deliver a therapeutic substance, e.g., one or more selected from the group consisting of proteins, naturally occurring or synthetic organic molecules, nucleic acid molecules, for example DNA or RNA, and a viral particle, prodrug, or nucleic acid molecule such as antisense nucleic acid molecules, the precursors may be reacted in those therapeutic substance's presence.

These exemplified materials may be formed in situ by simple addition of the reactants or precursors to the delivery device, e.g., a catheter, with or without an accelerator, and moving them to the implant for final reaction.

In addition to the filler materials that are placed in the bladder to "fill out the form" so to speak, additional materials may be placed in the bladder volume to allow visibility or detectability of the bladder shape or location. For instance, radiopaque materials allow visibility in fluoroscopes. Other types of opacifiers enhance detectability using, e.g., ultrasound.

Suitable and widely used liquid radiopacifiers include metrizamide (see U.S. Pat. No. 3,701,771) and iopromide (see U.S. Pat. No. 4,364,921). Metrizamide is sold in a dilute form as "Amipaque" by Winthrop-Breon Laboratories, a division of Sterling Drug Inc. Iopromide is often sold in a dilute form under the tradename "Ultravist". Other radiopaque liquid radiopacifiers are known.

Suitable solid radiopaque materials comprise materials selected from the group consisting of barium sulfate, bismuth trioxide, bismuth carbonate, and one or more powdered metals selected from the group consisting of tungsten, tantalum, gold, ruthenium, rhodium, osmium, iridium, palladium, platinum, rhenium, and their mixtures. These materials are often milled to a very fine particle size, a size that may be suspended in a fluid filler material such as those shown just above.

Placement of the listed metallic materials, as well as other radio frequency absorbing materials such as various iron oxides or hydroxides, graphite, and amorphous carbon also allows the filler material to be used as a "target" for radio frequency loading or heating. That is to say that a filler containing such radio frequency absorbing materials will, when subjected to a suitable radio frequency emission, absorb the energy and become heated. Low frequency radio-energy (e.g., 400-550 kHz.) and microwave radio energy (900 MHz. to 2.75 GHz.) are commonly used on the human body and are suitable in this service although the microwave is much more efficient.

Such internal electromagnetic heating may be used in a variety of procedures depending variously upon the placement of the bladder in the body and the value of the resulting elevated temperature, to warm tissue in the manner of an immune response, to coagulate blood or collagenous tissue or other tissue, to desiccate tissue, to ablate tissue, or even to necrose or to carbonize tissue. The list of maladies in which elevated localized temperatures are used is quite extensive. For instance, elevated localized internal temperatures are used in the treatment of tumors and cysts and endometriosis and in sterilization of males and females, in the controllable production of emboli for occlusion of aneurysm, for remodeling of tissue (via shrinkage, bulking, reshaping or the like) in reforming female uro-genital structures, etc. Such higher temperatures may be used in curing biologic adhesives such as the polycyanoacrylates (PCA) with or without accelerators or catalysts. Although the level of power required and the frequency of the radio waves must be determined by the designer of a device according to the teachings here, where the filled bladder is designed for a particular treatment, such calculations and experiments are readily made and require but modest work.

As may be apparent, the radio energy is applied to the filler within the bladder using appropriate antenna placed inside or outside the body.

Finally, the filler material may contain bioactive, chemiactive, or radioactive compounds as desired in conjunction with the desired treatment.

The invention has been described in terms of examples. It is our intent that the various physical components found and shown with regard to those examples be combined in the ways that would be used by one of ordinary skill in the art to fill out a specific design.

We claim as our invention:

1. An inflatable, expandable implant suitable for implantation in a vascular aneurysm within a human body, comprising:
   a bladder comprising a bladder wall consisting essentially of non-elastic material; and
   a polymerizable filler material comprising a poly(ethylene glycol) material;
   wherein said bladder wall defines a volume for enclosing of the polymerizable filler material therein between,
   wherein the polymerizable filler material is adapted to cure to a viscoelastic solid or a viscoelastic liquid within the bladder volume,
   wherein said bladder wall has at least one bladder wall opening for introduction of the polymerizable filler material, and at least one closure for said at least one bladder wall opening for maintaining the polymerizable filler material within the volume after introduction of the polymerizable filler material into the volume,
   wherein the bladder wall is expandable to an expanded shape upon introduction of the polymerizable filler material into the volume,
   wherein at least a portion of the bladder wall is in apposition, on a side wall opposite the volume, to an elastic woven fabric layer,
   wherein said woven layer is not disposed within said bladder volume, and
   wherein the bladder wall maintains its expanded shape after the polymerizable filler material is cured in situ to provide a supporting structure for the vascular aneurysm.

2. The implant of claim 1 wherein the non-elastic material is selected from the group consisting of polyethylene terephthalate, polyvinylchloride, polyurethanes, polyolefins, polyamides, and fluoropolymers.

3. The implant of claim 1 wherein the non-elastic material is selected from the group consisting of polytetrafluoroethylene, poly(ethylene-chlorofluoroethylene), poly(fluorinated ethylene propylene), polyperfluoroalkoxy, polychlorotrifluoroethylene, polyvinylfluoride, polyvinylidenefluoride, and expanded polytetrafluoroethylene.

4. The implant of claim 1 wherein the polymerizable filler material comprises a copolymer of a first material being said poly(ethylene glycol) material and a second material having a strong nucleophile selected from the group consisting of a thiol or a group containing a thiol.

5. The implant of claim 1 further comprising a therapeutic substance disposed within the volume of the bladder wall.

6. The implant of claim 1 further comprising a radiopaque material disposed within the volume of the bladder wall.

7. The implant of claim 6 wherein the radiopaque material is selected from the group consisting of barium sulfate, bismuth trioxide, bismuth carbonate, a powdered metal and combinations thereof.

8. The implant of claim 7 wherein the powdered metal is selected from the group consisting of tungsten, tantalum, gold, ruthenium, rhodium, osmium, iridium, palladium, platinum, rhenium and combinations thereof.

9. The implant of claim 6 wherein the radiopaque material comprises a fluid radiopaque material.

10. The implant of claim 9 wherein the fluid radiopaque material is selected from the group consisting of iopromide, metrizamide and combinations thereof.

11. An inflatable, expandable implant suitable for implantation in a vascular aneurysm within a human body, comprising:
   a bladder comprising a bladder wall consisting essentially of polyurethane material; and
   a polymerizable filler material comprising a poly(ethylene glycol) material;
   wherein said bladder wall defines a volume for enclosing of the polymerizable filler material therein between,
   wherein the polymerizable filler material is adapted to cure to a viscoelastic solid or a viscoelastic liquid within the bladder volume,
   wherein said bladder wall has at least one bladder wall opening for introduction of the polymerizable filler material, and at least one closure for said at least one bladder wall opening for maintaining the polymerizable filler material within the volume after introduction of the polymerizable filler material into the volume,
   wherein the bladder wall is expandable to an expanded shape upon introduction of the polymerizable filler material into the volume,
   wherein at least a portion of the bladder wall is in apposition, on a side wall opposite the volume, to a woven fabric layer,
   wherein said woven layer is not disposed within said bladder volume, and
   wherein the bladder wall maintains its expanded shape after the polymerizable filler material is cured in situ to provide a supporting structure for the vascular aneurysm.

* * * * *